(12) United States Patent
Tam

(10) Patent No.: US 10,859,559 B1
(45) Date of Patent: Dec. 8, 2020

(54) GEMSTONE TESTING APPARATUS

(71) Applicant: Jubilee Diamond Instrument(s) Pte. Ltd., Singapore (SG)

(72) Inventor: Kui Lim Tam, Singapore (SG)

(73) Assignee: Jubilee Diamond Instrument(s) Pte. Ltd., Singapore (SG)

( * ) Notice: Subject to any disclaimer, the term of this patent is extended or adjusted under 35 U.S.C. 154(b) by 0 days.

(21) Appl. No.: 16/988,914

(22) Filed: Aug. 10, 2020

Related U.S. Application Data

(63) Continuation of application No. PCT/SG2020/050247, filed on Apr. 21, 2020.

(30) Foreign Application Priority Data

Jun. 19, 2019 (GB) .................................. 1908754.3

(51) Int. Cl.
*G01N 25/18* (2006.01)
*G01N 33/38* (2006.01)
*G01N 21/88* (2006.01)
*F21V 8/00* (2006.01)
*G01N 27/04* (2006.01)

(52) U.S. Cl.
CPC ....... *G01N 33/381* (2013.01); *G01N 21/8806* (2013.01); *G01N 25/18* (2013.01); *G01N 27/041* (2013.01); *G02B 6/0005* (2013.01); *G01N 2021/8845* (2013.01); *G01N 2201/0221* (2013.01)

(58) Field of Classification Search
CPC ....... G01N 33/381; G01N 21/87; G01N 25/18
See application file for complete search history.

(56) References Cited

U.S. PATENT DOCUMENTS

| | | |
|---|---|---|
| 2,789,430 A | 4/1957 | Sinclaire |
| 4,255,962 A | 3/1981 | Ashman |
| 4,344,315 A | 8/1982 | Moxon et al. |
| 4,364,677 A | 12/1982 | Ashman |
| 4,394,580 A | 7/1983 | Gielisse |
| 4,488,821 A | 12/1984 | Wenckus |
| 5,164,586 A | 11/1992 | Hohberg et al. |
| 5,801,819 A | 9/1998 | Spear et al. |
| 5,835,205 A | 11/1998 | Hunter et al. |

(Continued)

FOREIGN PATENT DOCUMENTS

| | | |
|---|---|---|
| JP | 2015194467 | 11/2015 |
| WO | 8001414 | 7/1980 |

(Continued)

OTHER PUBLICATIONS

Gems & Gemology; Article entitled: "Synthetic Moissanite: A New Diamond Substitute", published Winter 1997, 16 pgs.

(Continued)

*Primary Examiner* — Maurice C Smith
(74) *Attorney, Agent, or Firm* — Taylor English Duma LLP

(57) ABSTRACT

The application provides an improved gemstone testing apparatus for testing a gemstone specimen. The gemstone testing apparatus includes a handheld casing, a processor unit, a first gemstone test device, a second gemstone test device, and a display unit. The first gemstone test device includes a first test probe and a thermal conductivity test module. The second gemstone test device includes a second test probe and a light absorption module.

20 Claims, 21 Drawing Sheets

(56) References Cited

U.S. PATENT DOCUMENTS

Figure 1:
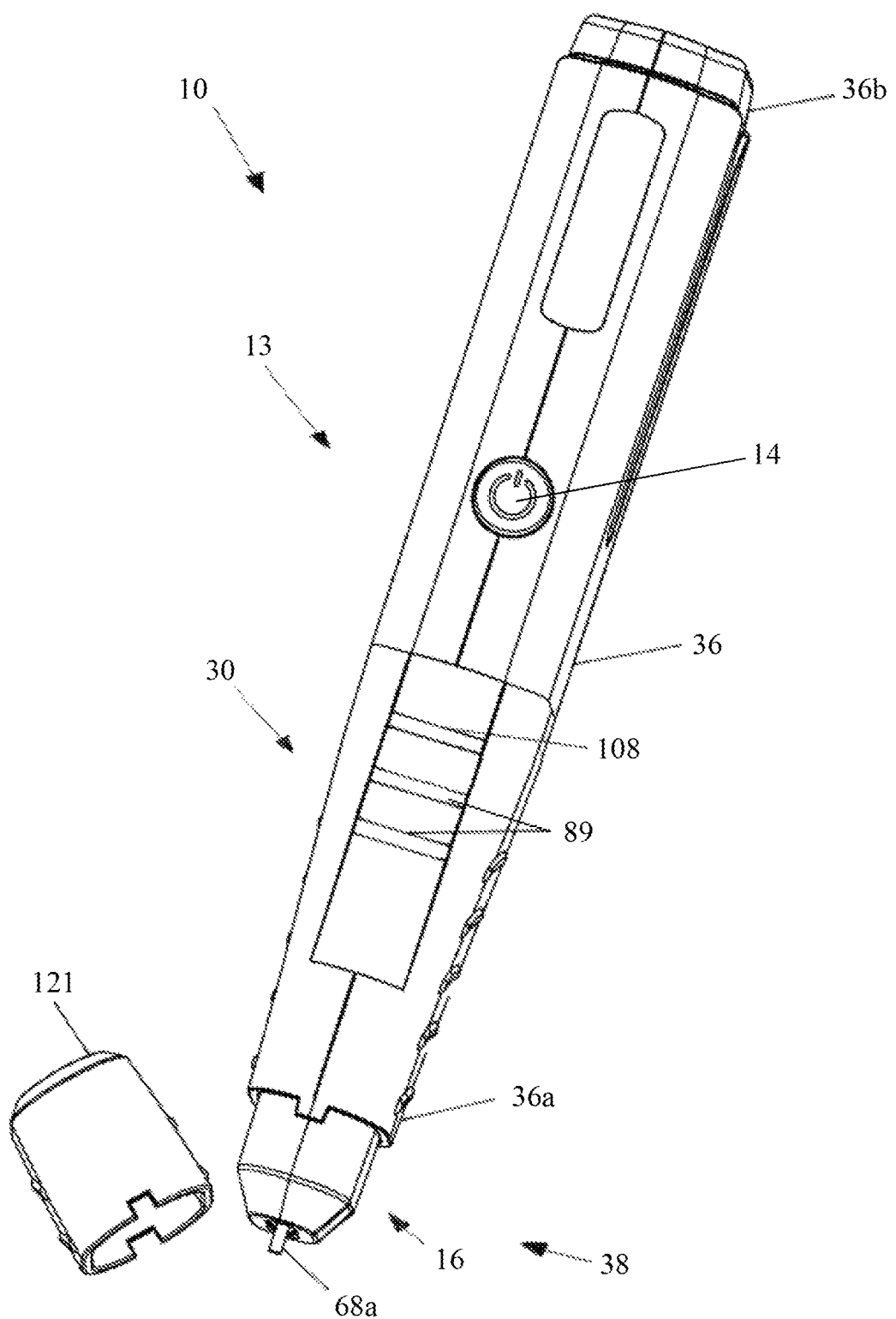

| | | | |
|---|---|---|---|
| 5,883,389 A | 3/1999 | Spear et al. | |
| 5,955,735 A | 9/1999 | Coleman | |
| 6,043,742 A * | 3/2000 | Austin | G01N 21/87 250/461.1 |
| 6,265,884 B1 * | 7/2001 | Menashi | G01N 27/041 324/693 |
| 6,439,766 B1 | 8/2002 | Nelson | |
| 7,105,822 B1 | 9/2006 | Beesley | |
| 7,126,351 B2 | 10/2006 | Claus | |
| 7,259,839 B2 | 8/2007 | Sivovolenko | |
| 7,362,109 B2 | 4/2008 | Loginov | |
| 7,382,445 B2 | 6/2008 | Sasian et al. | |
| 8,278,906 B2 | 10/2012 | Loginov et al. | |
| 8,564,316 B2 | 10/2013 | Kessler et al. | |
| 8,749,253 B2 | 6/2014 | Kessler et al. | |
| 8,760,758 B2 | 6/2014 | Verboven et al. | |
| 9,176,068 B1 | 11/2015 | Radomyshelsky et al. | |
| 9,395,350 B2 | 7/2016 | Kessler et al. | |
| 10,161,878 B2 | 12/2018 | Tam | |
| 10,228,330 B2 | 3/2019 | Tam | |
| 10,247,677 B2 | 4/2019 | Tam | |
| 2001/0023925 A1 | 9/2001 | Smith | |
| 2004/0008888 A1 | 1/2004 | Patton et al. | |
| 2005/0213203 A1 | 9/2005 | Harrison et al. | |
| 2006/0044823 A1 | 3/2006 | Wong et al. | |
| 2006/0087306 A1 | 4/2006 | Loginov | |
| 2006/0098187 A1 | 5/2006 | Claus | |
| 2012/0007619 A1 | 1/2012 | Zhu et al. | |
| 2012/0049836 A1 * | 3/2012 | Kessler | G01N 33/24 324/71.1 |
| 2012/0059619 A1 | 3/2012 | Zhu et al. | |
| 2012/0274751 A1 | 11/2012 | Smith et al. | |
| 2014/0337035 A1 | 11/2014 | Kessler et al. | |
| 2015/0015877 A1 | 1/2015 | Smith et al. | |
| 2015/0091593 A1 | 4/2015 | Zhu et al. | |
| 2015/0219567 A1 | 8/2015 | Sim et al. | |
| 2016/0178168 A1 | 6/2016 | Didur | |
| 2016/0178530 A1 * | 6/2016 | Davies | G01N 21/39 209/578 |
| 2016/0290930 A1 | 10/2016 | Takahashi | |
| 2016/0363576 A1 * | 12/2016 | Zhu | G01N 33/381 |
| 2018/0238811 A1 * | 8/2018 | Tam | G01J 1/44 |
| 2019/0011373 A1 | 1/2019 | Tam | |
| 2019/0072495 A1 | 3/2019 | Tam | |
| 2020/0249176 A1 | 8/2020 | Tam | |

FOREIGN PATENT DOCUMENTS

| | | |
|---|---|---|
| WO | 2014055041 | 4/2014 |
| WO | 2015007873 | 1/2015 |
| WO | 2017025825 | 2/2017 |
| WO | 2017208053 | 12/2017 |
| WO | 2018150221 | 8/2018 |
| WO | 2018220572 | 12/2018 |
| WO | 2019122955 | 6/2019 |

OTHER PUBLICATIONS

Gems & Gemology; Symposium proceedings issue entitled: "Proceedings of the Third International Gemological Symposium", published Fall 1999, 185 pgs.

Tam, Kui Lim; International Preliminary Report for Patentability for PCT/IB2016/054071, filed Jul. 7, 2016, dated Nov. 28, 2017, 4 pgs.

Tam, Kui Lim; International Search Report and Written Opinion for PCT/IB2016/054071, filed Jul. 7, 2016, dated Oct. 26, 2016, 11 pgs.

Tam, Kui Lim; Issue Notification for U.S. Appl. No. 15/751,529, filed Feb. 9, 2018, dated Dec. 5, 2018, 1 pg.

Tam, Kui Lim; Notice of Allowance for U.S. Appl. No. 15/751,529, filed Feb. 9, 2018, dated Oct. 3, 2018, 13 pgs.

Tam, Kui Lim; Notice of Allowance for U.S. Appl. No. 15/751,529, filed Feb. 9, 2018, dated Aug. 23, 2018, 14 pgs.

Tam, Kui Lim; Supplemental Notice of Allowance for U.S. Appl. No. 15/751,529, filed Feb. 9, 2018, dated Sep. 11, 2018, 12 pgs.

Tam, Kui Lim; Issue Notification for U.S. Appl. No. 16/176,059, filed Oct. 31, 2018, dated Mar. 13, 2019, 1 pg.

Tam, Kui Lim; Non-Final Office Action for U.S. Appl. No. 16/176,059, filed Oct. 31, 2018, dated Dec. 27, 2018, 15 pgs.

Tam, Kui Lim; Notice of Allowance for U.S. Appl. No. 16/176,059, filed Oct. 31, 2018, dated Feb. 6, 2019, 12 pgs.

Tam, Kui Lim; International Preliminary Report on Patentability for PCT/IB2016/053208, filed Jun. 1, 2016, dated Oct. 11, 2018, 7 pgs.

Tam, Kui Lim; International Search Report for PCT/IB2016/053208, filed Jun. 1, 2016, dated Feb. 28, 2017, 3 pgs.

Tam, Kui Lim; Issue Notification for U.S. Appl. No. 16/128,610, filed Sep. 12, 2018, dated Feb. 20, 2019, 1 pg.

Tam, Kui Lim; Non-Final Office Action for U.S. Appl. No. 16/128,610, filed Sep. 12, 2018, dated Nov. 13, 2018, 19 pgs.

Tam, Kui Lim; Notice of Allowance for U.S. Appl. No. 16/128,610, filed Sep. 12, 2018, dated Jan. 4, 2019, 7 pgs.

Tam, Kui Lim; International Search Report and Written Opinion for PCT/IB2017/050803, filed Feb. 14, 2017, dated Oct. 25, 2017, 14 pgs.

Tam, Kui Lim; International Search Report and Written Opinion for PCT/IB2017/058093, filed Dec. 19, 2017, dated Sep. 19, 2018, 12 pgs.

Zeiss; Article entitled: "Education in Microscopy and Digital Imaging", published as early as Dec. 23, 2008, located at <https://web.archive.org/web/20081223034455/http://zeiss-campus.magnet.fsu.edu/articles/lightsources/tungstenhalogen.html>, 9 pgs.

Tam, Kui Lim; International Preliminary Report on Patentability for PCT/IB2018/053881, filed May 31, 2018, dated Aug. 7, 2019, 4 pgs.

Tam, Kui Lim; International Search Report and Written Opinion for PCT/IB2018/053881, filed May 31, 2018, dated Oct. 29, 2018, 20 pgs.

* cited by examiner

GEMSTONE TESTING APPARATUS

CROSS-REFERENCE TO RELATED APPLICATIONS

This application is a continuation of PCT Patent Application PCT/SG2020/050247, filed Apr. 21, 2020, entitled "GEMSTONE TESTING APPARATUS," and designating the United States, which claims the benefit of United Kingdom Patent Application No. 1908754.3, filed Jun. 19, 2019, and entitled "Gemstone testing apparatus," each of which is incorporated herein in its entirety by these references for all purposes.

The application relates to an apparatus for testing gemstones, such as simulants, diamonds, and moissanite.

The diamond includes a native crystalline carbon that is very hard. The diamond can have a colour or be colourless. When the diamond is transparent and free from flaws, it is highly valued as jewellery. It is often used industrially as an abrasive.

The moissanite refers to a silicon carbide mineral and to its various crystalline polymorphs. The silicon carbide mineral can be found in nature, although this is rare. It can also be synthesized in the laboratory.

The synthetic moissanite, which is colourless or near colourless, resembles a diamond in many aspects, such as visual characteristics, hardness, and thermal conductivity, among other physical properties. Therefore, synthetic moissanite is widely used as a diamond simulant in today's jewellery market.

A gemstone tester is often considered as a convenient tool for identifying gemstones, such as diamonds, moissanite, and other precious stones. The gemstone tester can include a testing probe for determining thermal conductivity or electrical conductivity of the gemstone in order to classify the gemstone according to the thermal and electrical conductivity.

Prior art document US 20160363576 A1 discloses a multi-functional precious stone testing apparatus. The apparatus includes a portable housing, a testing unit, and an indication unit. The portable housing includes a hand-held casing and a probe casing. The probe casing extends from a front end of the hand-held casing. The testing unit includes a conductive probe. The conductive probe has a testing end portion that extends out of a tip end of the probe casing. The indication unit includes a LED (Light Emitting Diode) light unit. The LED light unit is placed in the hand-held casing. The LED light unit is also positioned away from the tip end of the probe casing. Functionally, the conductive probe is intended for contacting a testing object to determine the conductivity of the testing object. The LED light unit, which is received in the hand-held casing, is used for illuminating the testing end portion of the conductive probe during testing.

The LED light unit is positioned away from the tip end of the probe casing. The LED light unit generates heat, wherein it acts to prevent this heat from being transmitted toward the conductive probe.

The heat can affect the accuracy of measurement for the conductivity of the testing object.

Prior art document U.S. Pat. No. 6,043,742 A discloses an apparatus for detecting man-made gemstones using an alternating current conducted through a sample gemstone. The apparatus includes a hand-held housing in which is disposed electronic circuitry, a probe which extends from the housing, and a transmitting stimulus electrode in the form of a body-contact touchpad. The electronic circuitry comprises a filter for eliminating non-transmitted signals sensed by the probe. In use, the operator probes the gemstone by touching the conductive probe to the gemstone in an attempt to sense signals conducted through the gemstone. The electronic circuitry is used for producing an alternating current signal, preferably in sine waveform, for delivery to the touchpad. The alternating current signal is transmitted through the operator of the apparatus into the sample gemstone. An alarm is activated upon the detection of the conducted transmitted signal, indicating that the gemstone is human made.

It is an objective of the application to provide an improved gemstone testing apparatus.

An improved gemstone testing apparatus with a light intensity test is provided for testing a gemstone specimen. The light intensity test is also called a light absorption test.

The testing of the specimen is done to identify the material of the specimen. Examples of the gemstone specimen are diamond and moissanite. The gemstone test apparatus serves as a light absorption test device.

A thermal conductivity test is often used to separate diamond and moissanite gemstones from all other gemstones. Thereafter, the light absorption gemstone testing apparatus can be used to differentiate between a diamond and a moissanite gemstone.

The light absorption gemstone testing apparatus comprises a handheld casing, a plurality of light sources, a test probe, a photodetector, a processor unit, and a display unit.

The light sources, a part of the test probe, the photodetector, and the processor are often placed inside the handheld casing. The display unit is often placed on an outer surface of the handheld casing.

The handheld casing acts to contain and protect the inner parts of the light absorption gemstone testing apparatus. The shape of the handheld casing is designed for allowing a user to hold or carry the gemstone testing apparatus easily. The handheld casing can include grip indentations on an outer surface of the gemstone testing apparatus, thereby allowing the user to maintain a firm hold of the gemstone testing apparatus. The handheld casing is often made of plastic material to reduce weight and cost.

A first end of the test probe is placed outside the handheld casing. A second end of the test probe is often placed inside the handheld casing. In other words, the test probe protrudes from one part of the handheld casing.

The plurality of light sources is placed on at least two sides of the test probe. The multiple light sources are provided for emitting ultraviolet (UV) light rays with predetermined wavelengths. The light sources are inclined at a predetermined angle in order to direct the light rays towards an area that is in the vicinity of the first end of the test probe. UV light rays normally refer to electromagnetic radiation with a wavelength from about 10 nanometres (nm) to about 400 nm, although the workable range can be narrower. The working range of the UV light rays can extend from about 300 nm to about 400 nm.

The specimen is intended to be placed at this area for receiving the light rays. If the specimen is a diamond, it will reflect the light rays. If the specimen is a moissanite gemstone, it will absorb the light rays. In other words, the moissanite gemstone essentially will not reflect the light rays.

In use, the test probe is placed near the specimen. The first end of the test probe is adapted for receiving light rays from the specimen, which is illuminated by light rays from the multiple light sources. The test probe then transmits these light rays to the second end of the test probe.

The test probe is often provided with a light guide.

In one implementation, the light guide refers to an optical fibre. One end of the test probe is intended to receive light rays. The optical fibre then directs the light rays to another end of the test probe.

The optical fibre refers to a flexible, transparent fibre or strand, which is made of glass or plastic. The strand often has a very small diameter and it has two ends which allow transmission of light rays from one end to the other end. The diameter of the optical fibre is often slightly larger than a diameter of a human hair.

In another implementation, the light guide refers to a tube with a reflective inner surface. One end of the test probe is intended to receive light rays. An inner surface of the tube then reflects and directs the light rays to another end of the test probe.

The photodetector is often placed near the second end of the test probe. The photodetector is arranged to detect light rays from the light sources with the predetermined wavelengths. These light rays travelled from the specimen to the first end, to the second end of the light guide of the test probe, and to the photodetector. The photodetector is also arranged to measure the light intensity of these light rays.

The processor unit of an electronic testing unit is electrically connected to the plurality of light sources and to the photodetector. The processor unit is provided for determining a material of the gemstone in accordance with a measurement of the light intensity of the light rays. In other words, the processor unit determines whether the specimen comprises a diamond or a moissanite gemstone.

If the processor unit determines that the specimen reflects light rays, then the processor unit considers that the specimen is a diamond. On the other hand, if the processor unit determines that the specimen does not reflect light rays, the processor unit then considers that the specimen is moissanite.

The display unit is electrically connected to the processor unit. The display unit is used for receiving data regarding the determination of the material of the gemstone specimen from the processor unit. The display unit then shows or displays this data.

The plurality of light sources provides different benefits.

The arrangement of the multiple light sources allows a table of the specimen to receive light rays while the test probe is placed at different parts of the table of the specimen, even the test probe is at an edge of the table. The table refers to a facet or a flat side of a cut gemstone specimen, the facet being located at the top of the gemstone specimen. This facet is often the largest facet of the gemstone specimen.

In practice, the size of the test probe is often smaller than the size of the table of the specimen. A user may place the test probe at different parts of the table of the specimen.

When the test probe is placed substantially near or at the central location of the table, the table of the specimen will receive light rays emitted from all multiple light sources.

When the test probe is not placed substantially near the central location of the table of the specimen, such as at the edge of the table, the table of the specimen will still receive light rays emitted from one or more of the multiple light sources.

In short, the multiple light sources allow the specimen to receive sufficient light rays for testing the specimen, even when the test probe is placed at different parts of the table of the gemstone. The user is not restricted to place the test probe at the centre of the table in order to obtain an accurate gemstone test result.

This is different from other gemstone testers, wherein each gemstone tester includes a test probe and just one single light source being placed at one side of the test probe.

When the test probe is placed near or at a central location of a table of a specimen, the table of the specimen will receive light rays from the single light source.

When the test probe is placed at an edge of the table of the specimen, only a side facet of the specimen may receive light rays from the single light source. In other words, no light rays or little light rays are directed onto the table of the specimen.

The table of the specimen may then not receive enough light rays for testing the specimen. This then degrades or affects the testing to the specimen.

The light absorption gemstone testing apparatus can have different aspects.

In one implementation, the plurality of light sources of the light absorption gemstone testing apparatus comprises two light sources, although it can also comprise three or more light sources.

In a further implementation, the plurality of light sources is arranged around the test probe in a symmetric manner. In other words, the multiple light sources serve as similar parts that face each other or around a longitudinal axis of the test probe. In one example, two light sources are placed at two opposing sides of the test probe.

Each of the light sources is often inclined at a predetermined angle with respect to the longitudinal axis of the test probe.

The light absorption gemstone testing apparatus often includes a pressure switch and a pressure transmitting means.

In use, the test probe is brought in contact with a gemstone specimen, and it is pressed against a table or a surface of the gemstone specimen. The table refers to a facet of the gemstone specimen. The pressing serves to transfer a force from the gemstone specimen to the test probe. The pressure transmitting means acts to transfer the force from the test probe to the pressure switch. Upon receiving the force from the pressure transmitting means, the pressure switch then transmits a signal to activate or power up the processor unit of the gemstone testing apparatus. The activated processor unit thereafter provides electrical power to the multiple light sources for illuminating the gemstone specimen for testing the specimen.

The pressure-switch, together with the pressure transmitting means, allows the multiple light sources to be powered up only when the gemstone testing apparatus is activated by the test probe pressing against the gemstone specimen.

This is different from other gemstone testers that are powered up when these gemstone testers are switched on. These gemstone testers can be powered up when their test probes are not pressing against a gemstone specimen.

This activating of the gemstone test apparatus by the pressing of the test probe serves to save power. This is because other gemstone testers can be powered up when their test probes are not pressing against a gemstone specimen. In other words, the other gemstone testers can be powered up when their test probes are both pressing and not pressing against a gemstone specimen. This feature is especially important when the gemstone testing apparatus is powered by a battery, which has a predetermined limit of energy storage capability.

Moreover, this activating of the gemstone test apparatus by the pressing of the test probe acts to prevent accidental activation of testing of the gemstone specimen in that the gemstone testing is done when the test probe is not placed against the gemstone specimen.

As an example, the pressure transmitting means comprises an actuator member that comprises a rod-like member. The rod-like member can also operate with a spring member. In use, when the actuator member is moved by the test probe, the actuator member shifts towards the pressure switch, wherein the actuator member pushes an on/off button of the pressure switch for activating the processor unit of the gemstone testing apparatus.

In one implementation, the pressure switch is provided in the form of a thin film pressure sensor. The pressure sensor detects the pressing of the test probe on the gemstone specimen and sends a corresponding signal to the processor unit for activating or powering up the processor unit in order to enable the gemstone testing apparatus to test the gemstone specimen.

In another implementation, the pressure switch is provided in the form of a micro-switch. The micro-switch is normally in an open position. Upon receiving a force from the pressure transmitting means, the micro-switch changes to a closed position. The micro-switch provides a switch position signal to the processor unit for activating or powering up the processor unit in order to enable the gemstone testing apparatus to test the gemstone specimen.

In one aspect of the application, the multiple light sources of the light absorption gemstone testing apparatus emit light rays with a fixed wavelength that is between about 315 nm and about 400 nm while the photodetector is configured to detect light rays with this fixed wavelength. In other words, the photodetector with a peak detection sensitivity that is suitable for detecting light rays with this fixed wavelength.

Alternatively, the light rays can also have different wavelengths that are between about 315 nm and about 400 nm. The photodetector is then configured to detect light rays with these different wavelengths.

In one specific implementation, the multiple light sources emit light rays with a fixed wavelength of about 365 nm. The photodetector is configured to detect light rays with this fixed wavelength of about 365 nm.

In a different implementation, the plurality of light sources is replaced with a ring light. The ring light is arranged to surround the test probe. The ring light is used for emitting light rays from different sides of the test probe, wherein the light rays are directed towards the gemstone specimen.

The light absorption gemstone testing apparatus often includes an external cap that is intended for attaching to the handheld casing in order to cover and to protect the test probe from being damaged.

In one variant of the light absorption gemstone testing apparatus, the external cap comprises a gemstone test reference tablet. In other variants of the light absorption gemstone testing apparatus, the gemstone test reference tablet is not present.

The gemstone test reference tablet is capable of reflecting light rays from the multiple light sources. In use, a user uses the gemstone test reference tablet to check the functions of the gemstone testing apparatus.

The light absorption gemstone testing apparatus often includes a power source unit for supplying electrical power to parts of the gemstone testing apparatus, such as the multiple light sources, the photodetector, the electronic testing unit, and the display unit.

The light absorption gemstone testing apparatus can provide gemstone test results to the user in different ways.

In one implementation, the display unit of the light absorption gemstone testing apparatus includes a plurality of indicator lights for providing visual indications of the gemstone test results. In other words, the display unit can include indicator lights or a display screen for emitting light rays to display data regarding the gemstone test results in a visual manner.

In another implementation, the light absorption gemstone testing apparatus further includes a buzzer or an audio speaker for generating an audio indication of the gemstone test result. An example of the audio indication includes a continuous or an intermittent beeping sound.

In another aspect of the application, the test probe includes a light guide. In one example, the light guide includes an optical fibre to reflect and direct light rays from one end to another end of the light guide. In another example, the light guide includes tube with a reflective inner surface. The reflective inner surface serves to reflect and direct light rays from one end to another end of the light guide. The optical fibre often has better light reflection properties than the reflective inner surface of a tube.

In one specific implementation, the light guide includes a hollow metal tube with an inner reflective surface. In another implementation, the light guide includes an optical fibre.

The optical fibre refers to a flexible, transparent fibre or strand, which is made of glass or plastic. The strand has a very small diameter and it has two ends which allow transmission of light rays between the two ends. The diameter of the optical fibre is often slightly larger than a diameter of a human hair.

The optical fibre having a small diameter allows can be used for receiving light rays from small and large gemstone specimens. The optical fibre is different from a probe tip with large diameter that is not suitable for touching a small specimen.

Furthermore, an improved method with a light intensity test is provided for differentiating between a diamond and a moissanite gemstone.

The method includes a process step of a user pressing a test probe of the light absorption gemstone testing apparatus against a table of a gemstone specimen. A force is then transmitted from the gemstone to the test probe and to a pressure switch of the gemstone testing apparatus.

After this, a plurality of light sources of the gemstone testing apparatus is activated for illuminating the gemstone specimen with light rays. The table of the gemstone specimen receives the light rays from at least one of the multiple light sources.

If the gemstone specimen is moissanite, the light rays are then absorbed. In other words, essentially no or little light rays are reflected from the moissanite. If the gemstone specimen is a diamond, the light rays are reflected toward the test probe. The intensity of the light rays being reflected from the gemstone specimen is then measured. A material of the gemstone is later determined in accordance with the measured light intensity.

The method can include a further step of providing an indication of the material of the gemstone specimen to a user.

In one implementation, said step of providing the indication of the material of the gemstone specimen comprises a plurality of light indicators providing a visual indication of the determined material of the gemstone specimen.

In another implementation, said step of providing the indication of the material of the gemstone specimen comprises a buzzer or speaker generating an audio indication of the determined material of the gemstone specimen.

Furthermore, a further improved gemstone testing apparatus with two light intensity tests is provided for testing a gemstone specimen.

The gemstone testing apparatus includes a handheld casing, a light module, a test probe, a photodetector, a processor unit, and a display unit.

The test probe is placed at one end of the handheld casing. A first end of the test probe is placed outside the handheld casing.

The light module is provided for emitting light rays towards an area that is in the vicinity of the first end. The first end is adapted for receiving light rays from the specimen and for transmitting the received light rays to a second end of the test probe.

The photodetector is arranged to measure the intensity of the light rays from the second end.

The processor unit is used for determining a material of the specimen in accordance with a measurement of the intensity of the light rays.

The display unit is used for displaying the gemstone test result to a user.

The light module includes at least two first light sources for emitting first light rays with a wavelength of about 365 nm for differentiating between a diamond gemstone specimen and a moissanite gemstone specimen.

The light module also includes at least two second light sources for emitting second light rays with a wavelength of about 254 nm for differentiating between a gemstone specimen from a first group consisting of type IaA, IaAB, and Ib diamonds and a gemstone specimen from a second group consisting of type IaB, IIa, and IIb diamonds.

The gemstone test apparatus provides several benefits.

The multiple first and second light sources allow a table of the specimen to receive light rays while the test probe is placed at different parts of the table of the specimen, even at an edge of the table. The table refers to a facet or a flat side of a cut gemstone specimen, the facet being located at the top of the gemstone specimen. This facet is often the largest facet of the gemstone specimen.

Further, this arrangement allows two different gemstone tests—one test using light rays with a wavelength of about 365 nm and the other test using light rays with a wavelength of about 254 nm—to be done with just one device and with just one contact of the gemstone specimen. The two gemstone tests can also be done one after another independently without human control.

These gemstone tests act to differentiate between a diamond gemstone and a moissanite gemstone and to differentiate between a gemstone specimen from a first group consisting of type IaA, IaAB, and Ib diamonds and a gemstone specimen from a second group consisting of type IaB, IIa, and IIb diamonds. These gemstone tests are often done automatically, one after another.

The first and the light sources are often arranged around the test probe in a symmetric manner for easy design of the test apparatus.

The gemstone testing apparatus often includes a pressure switch, and a pressure transmitting means for transferring a force from the test probe to the pressure switch, wherein the pressure switch activates the gemstone testing apparatus.

The pressure switch can include a thin film pressure sensor or a micro-switch for easy implementation.

The gemstone testing apparatus often comprises an external cap that can be attachable to the handheld casing for protecting the test probe.

Although the external cap can include a gemstone test reference tablet that is provided for checking functions of the gemstone testing apparatus, the external cap can also be provided without the gemstone test reference tablet.

The gemstone testing apparatus can also include a power source unit for supplying electrical power to the gemstone testing apparatus.

The display unit can include a plurality of indicator lights for providing visual indications of the gemstone test result to a user of the gemstone testing apparatus.

The gemstone testing apparatus can include a buzzer for providing an audio indication of the gemstone test result to the user.

The test probe can comprise a light guide with a reflective inner surface.

The light guide is used for directing light rays from the first and the second light sources to the gemstone specimen.

In one example, the light guide includes a hollow metal tube. The metal tube has an inner reflective surface for directing light rays.

In another example, the light guide includes an optical fibre, which acts to direct light rays.

The optical fibre can be inserted a metal tube, wherein the metal tube surrounds and protects the optical fibre.

Furthermore, an improved method with two light intensity tests is provided for testing a gemstone specimen. The light intensity test is also called a light absorption test.

The method includes a first light absorption test. The light absorption test is also called a light intensity test.

The first light absorption includes a step of pressing a test probe of a gemstone testing apparatus against the gemstone specimen.

A force is then transmitted from the test probe to a pressure switch of the gemstone testing apparatus.

A processor unit later activates two or more first light sources of the gemstone testing apparatus for emitting first light rays with a wavelength of about 365 nm to illuminate the gemstone specimen. The first light rays are intended to differentiate between a diamond gemstone and a moissanite gemstone.

The gemstone specimen later receives the first light rays from at least one first light source. In use, the user may position the gemstone specimen such that the gemstone specimen receives the first light rays from one or more first light sources.

A first light intensity of the first light rays, which are reflected from the gemstone specimen, is later measured.

After this, the processor unit determines a first category of the gemstone specimen in accordance with the measured first light intensity. The gemstone specimen is determined as to whether it is a diamond gemstone or a moissanite gemstone.

The method also includes a second light absorption test.

In a general sense, the second light absorption test can be done before or after the determination of the first light absorption test.

The second light absorption test is usually done automatically after the first light absorption test while the test probe is still contacting the gemstone specimen.

The processor unit often starts automatically the second light absorption test when the processor unit determines, in the first light absorption test, that the gemstone specimen a diamond gemstone.

The second light absorption test includes a step of the processor unit activating at least two second light sources of the gemstone testing apparatus for emitting second light rays with a wavelength of about 254 nm to illuminate the gemstone specimen. The second light rays are used to differentiate between a diamond gemstone from a first group consisting of type IaA, IaAB, and Ib diamonds and a diamond gemstone from a second group consisting of type IaB, IIa, and IIb diamonds.

The gemstone specimen later receives the second light rays from at least one second light source.

A second light intensity of the second light rays that are reflected from the gemstone specimen is afterwards measured.

The processor unit then determines a second category of the gemstone specimen in accordance with the measured second light intensity. The gemstone specimen is determined as to whether it is a diamond from the first group or a diamond from the second group.

The method often includes providing an indication of the material of the gemstone specimen to a user.

The provision of the indication of the material of the gemstone specimen can include providing a visual indication or an audio indication of the material of the gemstone specimen.

The application provides an improved combination gemstone testing apparatus for testing a gemstone specimen. The gemstone testing apparatus acts to determine which category of gemstone or jewel does the specimen falls under or belongs.

The gemstone testing apparatus includes a handheld casing, a processor unit, a first gemstone test device, a second gemstone test device, and a display unit.

The processor unit is enclosed in the handheld casing. A large part of the first gemstone test device and a large part of the second gemstone test device are also enclosed in the handheld casing. The display unit is placed on an outer surface of the handheld casing.

Referring to the first gemstone test device, it includes a first test probe and a thermal conductivity test module. The thermal conductivity test module is also called a heat conductivity test module.

The first test probe is used for contacting a table of the gemstone specimen. The table refers to a facet or a flat side of the gemstone specimen. This facet is often located at the top of the gemstone specimen and is often the largest facet of the gemstone specimen.

The thermal conductivity test module includes a heating element and a temperature measurement unit.

In use, the heating element is electrically connected to the first test probe and to the processor unit for heating the first test probe.

The first test probe is often heated unit until the thermal conductivity measurement reaches a predetermined value.

The temperature measurement unit is electrically connected to the first test probe for measuring a thermal conductivity of the specimen.

The processor unit is adapted to determine a first category of the specimen according to the thermal conductivity measurement. In other words, the processor unit determines whether the specimen falls under a category of simulant or under a category of a group consisting of diamond and moissanite. Examples of the simulant include not only cubic zirconia and sapphire but also other simulants.

In short, the thermal conductivity measurement enables the processor unit to differentiate between simulant and a group consisting of diamond and moissanite.

Referring to the second gemstone test device, it includes a second test probe and a light absorption module.

The second test probe is used for contacting the table of the specimen.

The light absorption module includes at least two first light sources, at least two second light sources, and a photodetector.

The first light sources are used for emitting ultraviolet first light rays with a wavelength of about 365 nm to illuminate an area that is in the vicinity of an outer end of the second test probe. These first light sources are provided adjacent to the second test probe.

The second test probe includes a light guide for receiving the first light rays that are reflected from the specimen. The light guide is also used for transmitting the first light rays to an inner end of the second test probe. In other words, the light guide directs the first light rays from the outer end to the inner end of the second test probe.

The photodetector is provided at the inner end of the second test probe to measure the light intensity of the first light rays, which emerge from the inner end of the second test probe.

The processor unit is adapted to determine a second category of the specimen according to the light intensity measurement of the first light rays.

In detail, the processor unit determines whether the specimen falls under a category of diamond that is colourless or near colourless or under a category of moissanite, according to the light intensity measurement of the first light rays. The colourless diamonds and the near colourless diamonds are defined according to the diamond colour chart, which is published by the Gemological Institute of America (GIA).

When the light intensity measurement of the first light rays falls above a first predetermined threshold limit, the processor unit determines or considers that the specimen falls under a category of diamond that is colourless or near colourless On the other hand, when the light intensity measurement of the first light rays falls below the first predetermined threshold limit, the processor unit determines that the specimen falls under a category of moissanite.

In short, the measurement of the first light rays allow the processor unit to differentiate between a diamond that is colourless or near colourless and a moissanite gemstone.

Similarly, the second light sources are used for emitting ultraviolet second light rays with a wavelength of about 254 nm to illuminate an area that is in the vicinity of the outer end of the second test probe. These second light sources are provided adjacent to the second test probe.

The light guide is used for receiving the second light rays that are reflected from the specimen. The light guide directs and guides the second light rays from the outer end to the inner end of the second test probe.

The photodetector then measures the light intensity of the second light rays, which emerge from the inner end of the second test probe.

The processor unit later determines a third category of the specimen according to the light intensity measurement of the second light rays.

Put differently, the processor unit determines whether the specimen falls under a first group consisting of type IaA, IaAB, and Ib diamonds or under a second group consisting of type IaB, IIa, and IIb diamonds.

The diamonds from the first group are extracted or mined from the ground. These diamonds are not subjected to enhancement using high-pressure and high temperature (HPHT) methods. On the other hand, the diamonds from the second group are either extracted or mined from the ground or are produced in the laboratory. These diamonds may be enhanced using HPHT methods. When the light intensity measurement of the second light rays falls below a second predetermined threshold limit, the processor unit determines that the specimen falls under the first group consisting of type IaA, IaAB, and Ib diamonds.

When the light intensity measurement of the second light rays above the second predetermined threshold limit, the processor unit determines that the specimen falls under the second group consisting of type IaB, IIa, and IIb diamonds.

In short, the measurement of the second light rays allow the processor unit to differentiate between a specimen that falls under a first group consisting of type IaA, IaAB, and Ib diamonds and a specimen that falls under a second group consisting of type IaB, IIa, and IIb diamonds.

With reference to the display unit, it is attached to the handheld casing for displaying a category of the gemstone specimen, which is determined by the processor unit. The category can refer to the first category, the second category, or the third category.

The combination gemstone testing apparatus allows a user to determine which category a gemstone specimen falls under using a single device. In practice, this is especially useful when the specimen can fall under several different categories.

The combination gemstone testing apparatus provides a test result of a gemstone specimen with confidence while allowing a user with no extensive training to determine which category the specimen belongs.

The gemstone testing apparatus also allows different test units, namely the thermal conductivity test unit and the light absorption test unit to share or use common parts, such as the computing processor unit and the display unit. This allows the gemstone testing apparatus to have lower cost and is easier to produce.

Several implementations of the combination gemstone testing apparatus are possible.

The first gemstone test device can include an electrical conductivity test module, although the first gemstone test device can also be provided without this module.

The electrical conductivity test module comprises a third light source and an electrical conductivity test circuit.

In use, the third light source emits UV third light rays with a wavelength of about 365 nm to illuminate an area that is in the vicinity of an outer end of the first test probe.

The electrical conductivity test circuit is electrically connected to the first test probe for measuring the electrical conductivity of the specimen.

The processor unit is adapted to determine a fourth category of the specimen according to the electrical conductivity measurement.

The processor unit determines whether the specimen falls under a category of most diamonds, which are colourless or near colourless, or under a category of most moissanite gemstones, according to the electrical conductivity measurement.

Most moissanite gemstones are electrically conductive while F1 moissanite gemstones have high electrical resistance. On the other hand, most diamonds, which are colourless or near colourless, are not electrically conductive while some lab-grown synthetic diamonds are electrically conductive.

In short, the electrical conductivity measurement allows the processor unit to differentiate between most diamonds, which are colourless or near colourless, and most moissanite gemstones.

The first test probe often protrudes from a transparent housing portion, which is provided at one end portion of the handheld casing.

The third light source of the first gemstone test device can emit light rays with a wavelength of between about 315 nm and about 425 nm.

In one implementation, the first light sources of the second gemstone test device comprise just two first light sources.

Similarly, the second light sources of the second gemstone test device include just two second light sources.

The first light sources are often arranged around the second test probe in a symmetric manner for ease of use and design.

Similarly, the second light sources can be arranged around the second test probe in a symmetric manner for ease of use and design.

The first light sources can emit light rays with a wavelength of between about 315 nm and about 400 nm.

In one variant, the second gemstone test device includes a pressure switch, and a pressure transmitting means for transferring a force from the second test probe to the pressure switch. The pressure switch then transmits a switch status signal for activating the second gemstone test device.

The pressure switch can include or refer to a thin film pressure sensor or to a micro-switch.

The light guide can include an optical fibre or a hollow metal tube.

The combination gemstone testing apparatus can include an external cap being attachable to the handheld casing for protecting the first test probe and the second test probe.

The external cap can include a gemstone test reference tablet that is provided for checking functions of the light absorption gemstone testing apparatus, although the external cap can also be provided without the gemstone test reference tablet.

The combination gemstone testing often includes a power source unit for supplying electrical power to the processor unit, the first gemstone test device gemstone testing apparatus, and the second gemstone test device gemstone testing apparatus.

The display unit can include a Liquid Crystal Display (LCD) display panel for displaying a category of the specimen, which is determined by the processor unit.

The combination gemstone testing apparatus can also include a buzzer for providing an audio indication of a category of the specimen, which is determined by the processor unit, to a user.

The application provides an improved method for testing a gemstone specimen.

The gemstone testing apparatus can be used to perform a thermal conductivity test, an electrical conductivity test, a first light absorption test, and a second light absorption test. The light absorption test is also called a light intensity test.

In another variant, the gemstone testing apparatus is provided without the electrical conductivity test.

The thermal conductivity test serves to differentiate between simulant and a group consisting of diamond and moissanite.

If the thermal conductivity test indicates that the specimen belongs to the group consisting of diamond and moissanite, the first light absorption test is often performed.

The first light absorption test acts to differentiate between diamond that is colourless or near colourless and moissanite.

If the first light absorption test indicates that the specimen is a diamond that is colourless or near colourless, then the second light absorption test is often performed.

The second light absorption test acts to differentiate between a specimen from a first group consisting of type IaA, IaAB, and Ib diamonds and a specimen from a second group consisting of type IaB, IIa, and IIb diamonds.

The steps of the method are described in detail below.

Steps for performing the thermal conductivity test are described below.

The thermal conductivity test comprises a process step of a user pressing a power on button on the casing to activate the heating element.

The heating element then heats the first test probe. This heating of the first test probe is often done such that the temperature of the test probe is maintained at a predetermined temperature.

After this, the user presses the outer end of the first test probe against the table of the gemstone specimen, thereby allowing the first test probe to transmit heat energy to the gemstone specimen.

After a predetermined period, the temperature measurement unit measures the thermal conductivity of the specimen by determining heat dissipation of the first test probe. The heat dissipation of the first test probe provides an indication of heat dissipation of the gemstone specimen.

The processor unit then determines whether the gemstone specimen falls under the category of simulant or under the category of a group consisting of diamond and moissanite according to the thermal conductivity measurement.

Steps for performing a first light absorption test are described below.

A message is often provided to the user for prompting the user to proceed with this light absorption test, when the processor unit determines that the gemstone specimen falls under the category of a group consisting of diamond and moissanite.

The first light absorption test includes a step of pressing the outer end of the second test probe against the table of the specimen.

This step of pressing can serve to activate the first light sources.

The first light sources then emit ultraviolet first light rays with a wavelength of about 365 nm to illuminate an area that is in the vicinity of an outer end of the second test probe, which also illuminate the gemstone specimen.

The gemstone specimen can reflect the first light rays back to the second test probe, which acts to guide the first light rays from the outer end to the inner end of the second test probe.

The photodetector later measures a light intensity of the reflected first light rays.

The processor unit then determines whether the specimen falls under the category of diamond that is colourless or near colourless or under the category of moissanite according to the light intensity measurement.

Steps for performing the second light absorption test are described below.

The second light absorption test is often automatically initiated when the processor unit determines that the specimen falls under the category of diamond that is colourless or near colourless.

While the outer end of the second test probe is still pressing against the table of the specimen, the second light sources is activated.

The second light sources then emit ultraviolet second light rays with a wavelength of about 254 nm to illuminate an area that is in the vicinity of an outer end of the second test probe, which also illuminate the gemstone specimen.

The gemstone specimen can reflect the second light rays back to the second test probe, which acts to guide the second light rays from the outer end to the inner end of the second test probe.

The photodetector later measures a light intensity of the reflected second light rays.

The processor unit then determines the specimen falls under a first group consisting of type IaA, IaAB, and Ib diamonds or under a second group consisting of type IaB, IIa, and IIb diamonds.

Steps for performing an electrical conductivity test is described below, although the method can be done without the electrical conductivity test.

The electrical conductivity test is often done directly after the heat conductivity test is performed.

The steps include activating a third light source to emit ultraviolet third light rays with a wavelength of about 365 nm illuminate an area that is in the vicinity of an outer end of the first test probe. This, in turn, serves to illuminate the gemstone specimen.

The electrical conductivity test circuit later measures the electrical conductivity of the specimen while the third light source is illuminating the gemstone specimen.

The processor unit then determines whether the specimen falls under the category of diamond or under the category of moissanite according to the electrical conductivity measurement.

An indication of the material of the gemstone specimen is often provided to a user.

In one aspect of the application, the provision of the indication of the material of the gemstone specimen comprises providing a visual indication of the material of the gemstone specimen.

In another aspect of the application, the provision of the indication of the material of the gemstone specimen comprises providing an audio indication of the material of the gemstone specimen.

Figure 2:
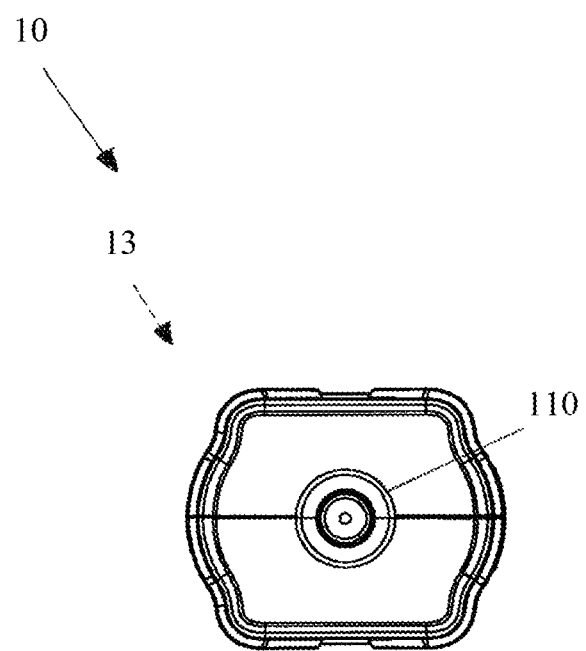
Figure 3:
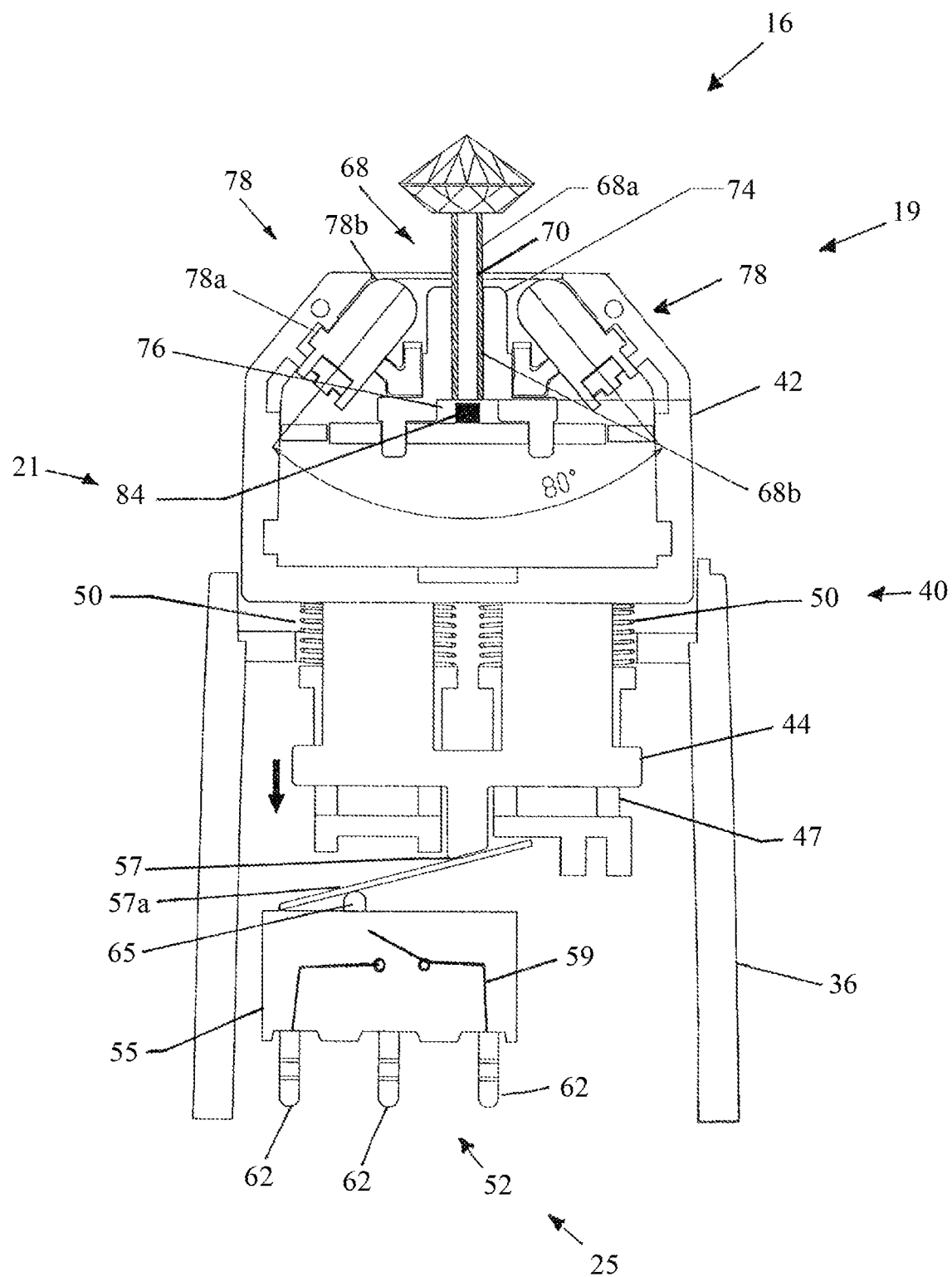
Figure 4:
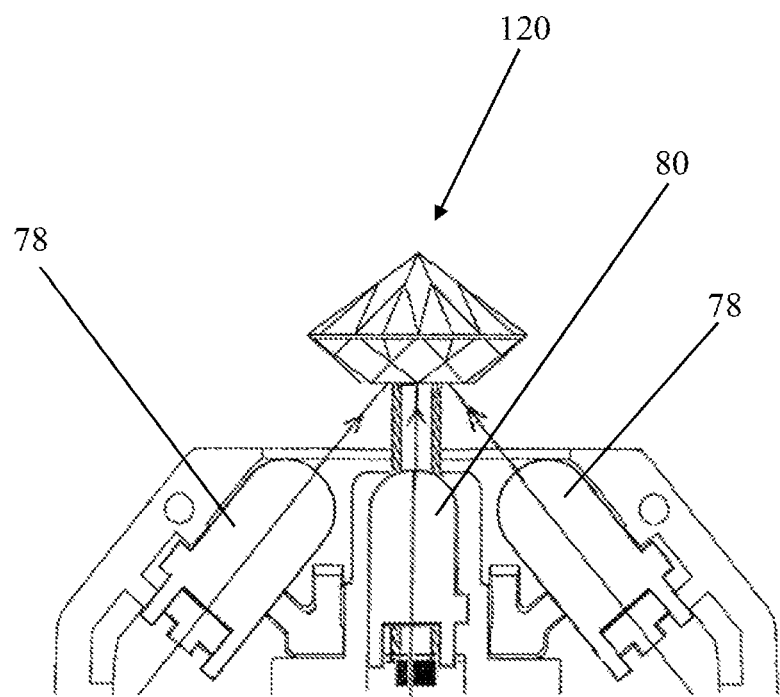
Figure 5:
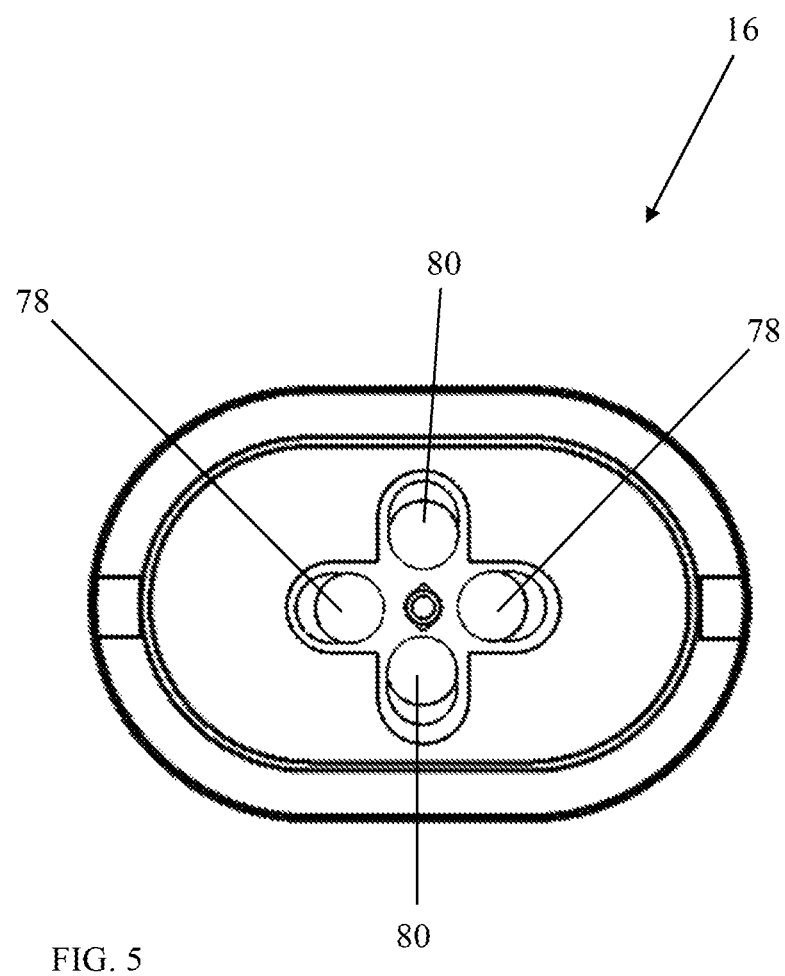
Figure 6:
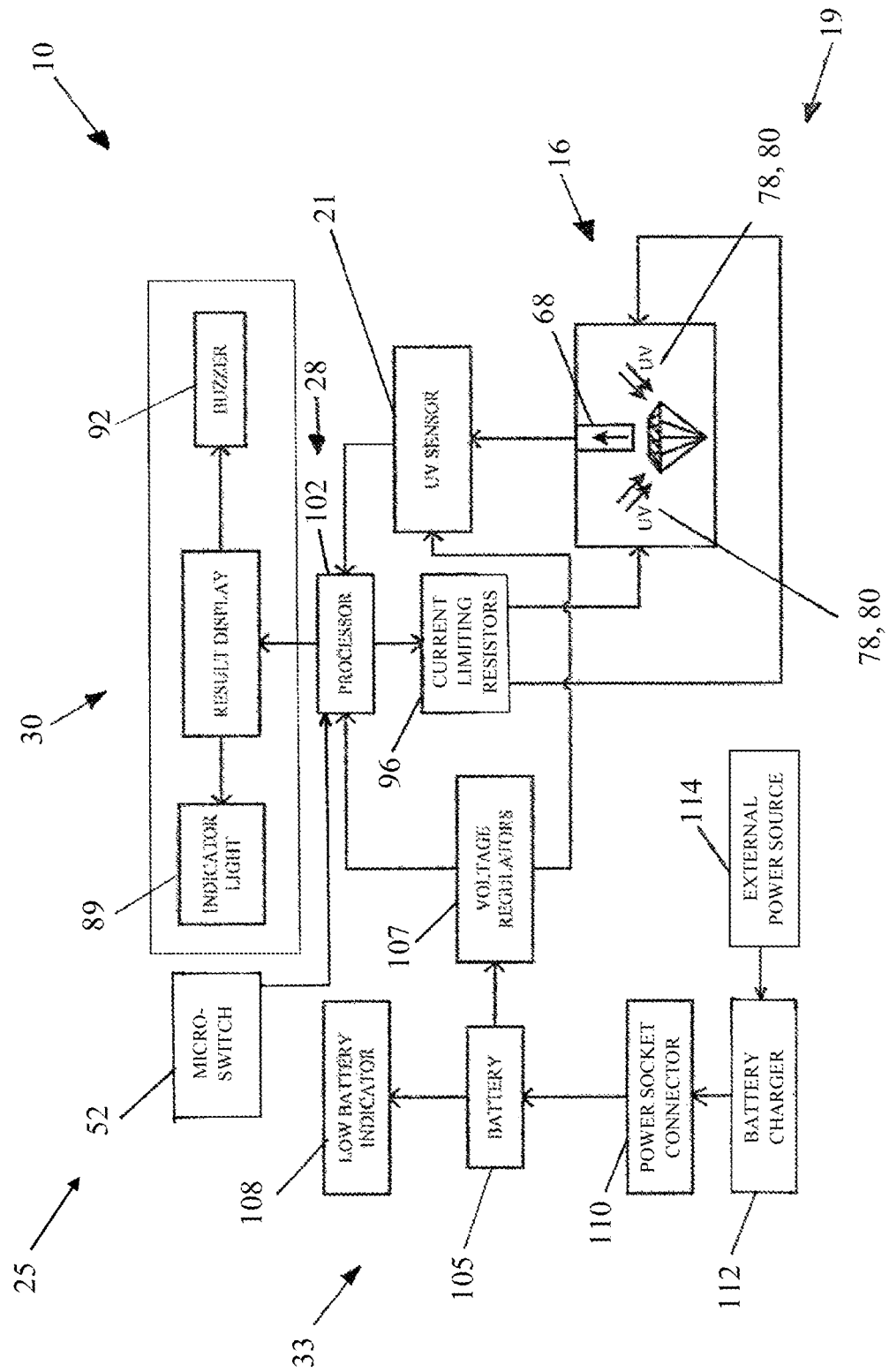
Figure 7:
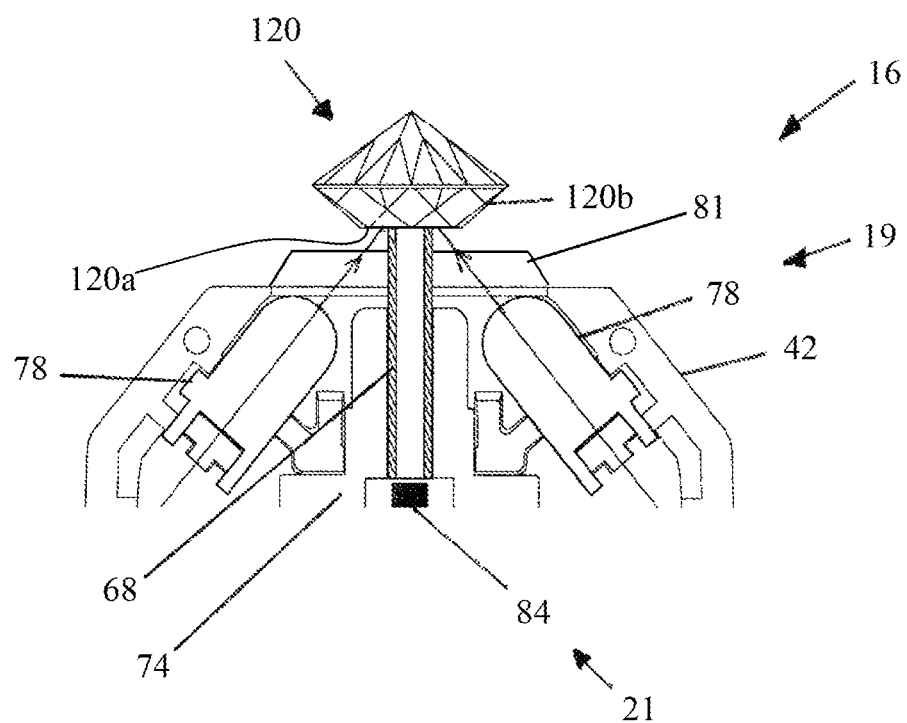
Figure 8:
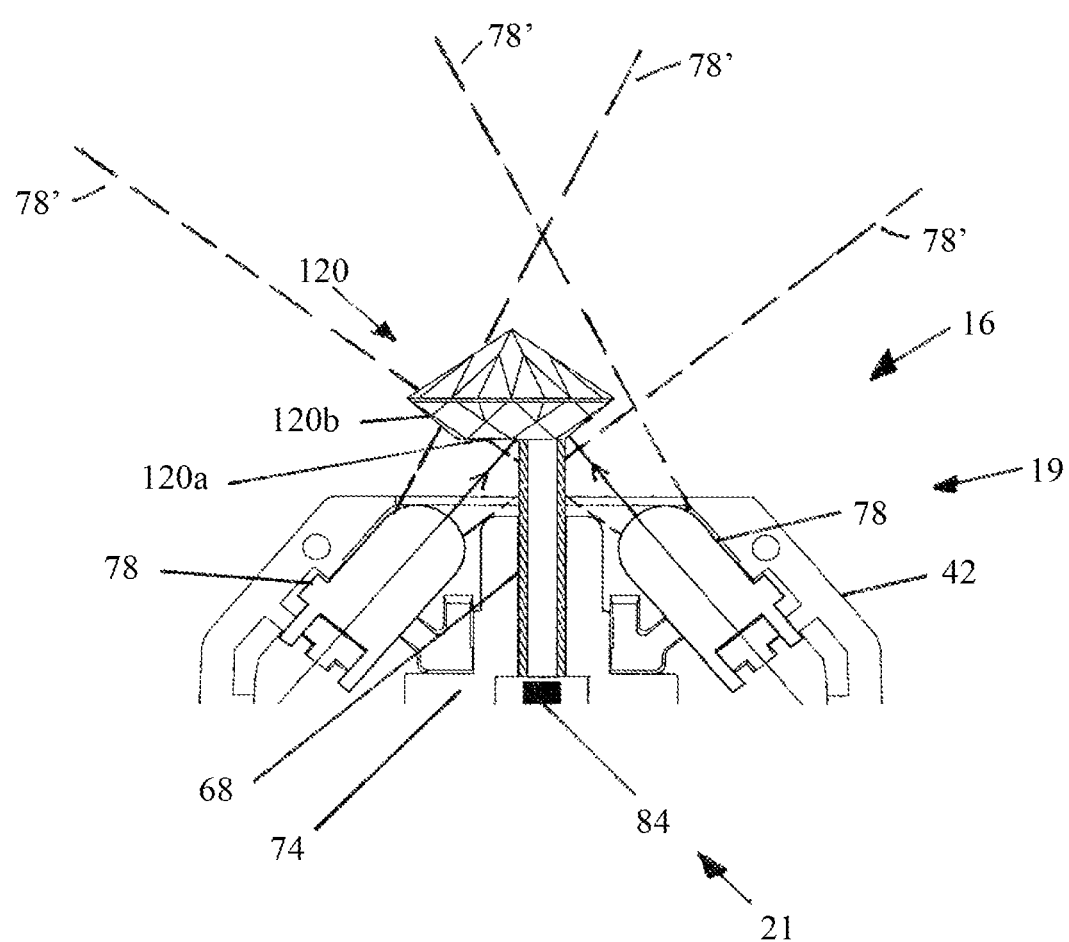
Figure 9:
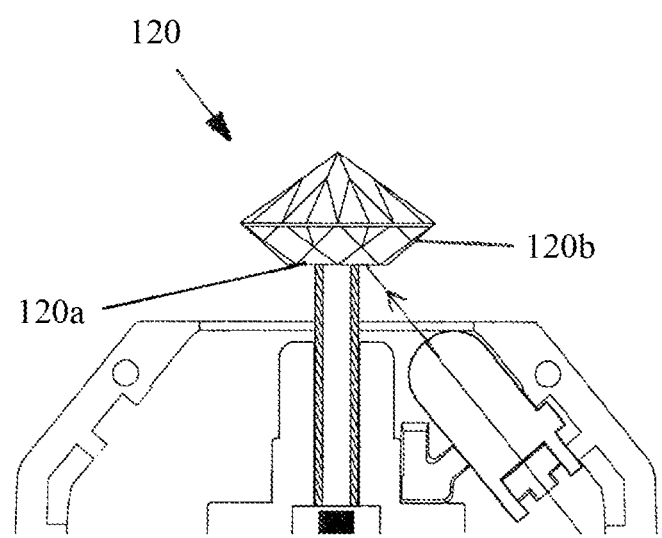
Figure 10:
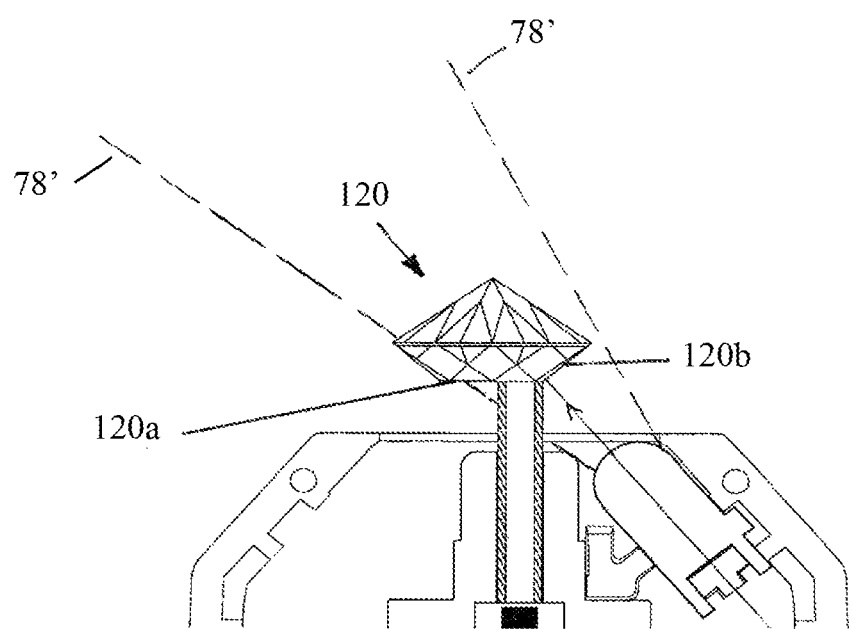
Figure 11:
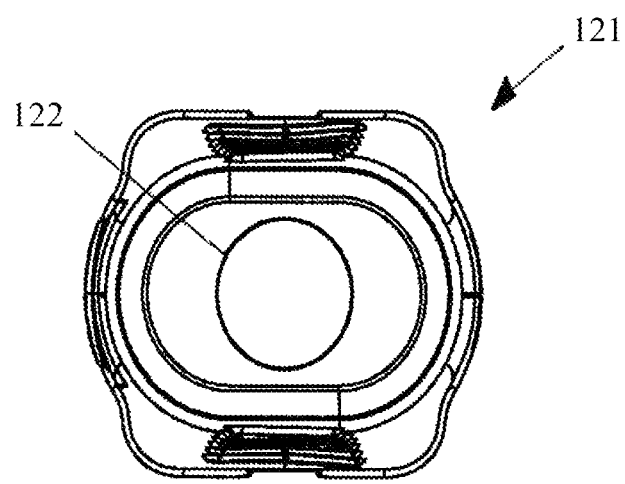
Figure 12:
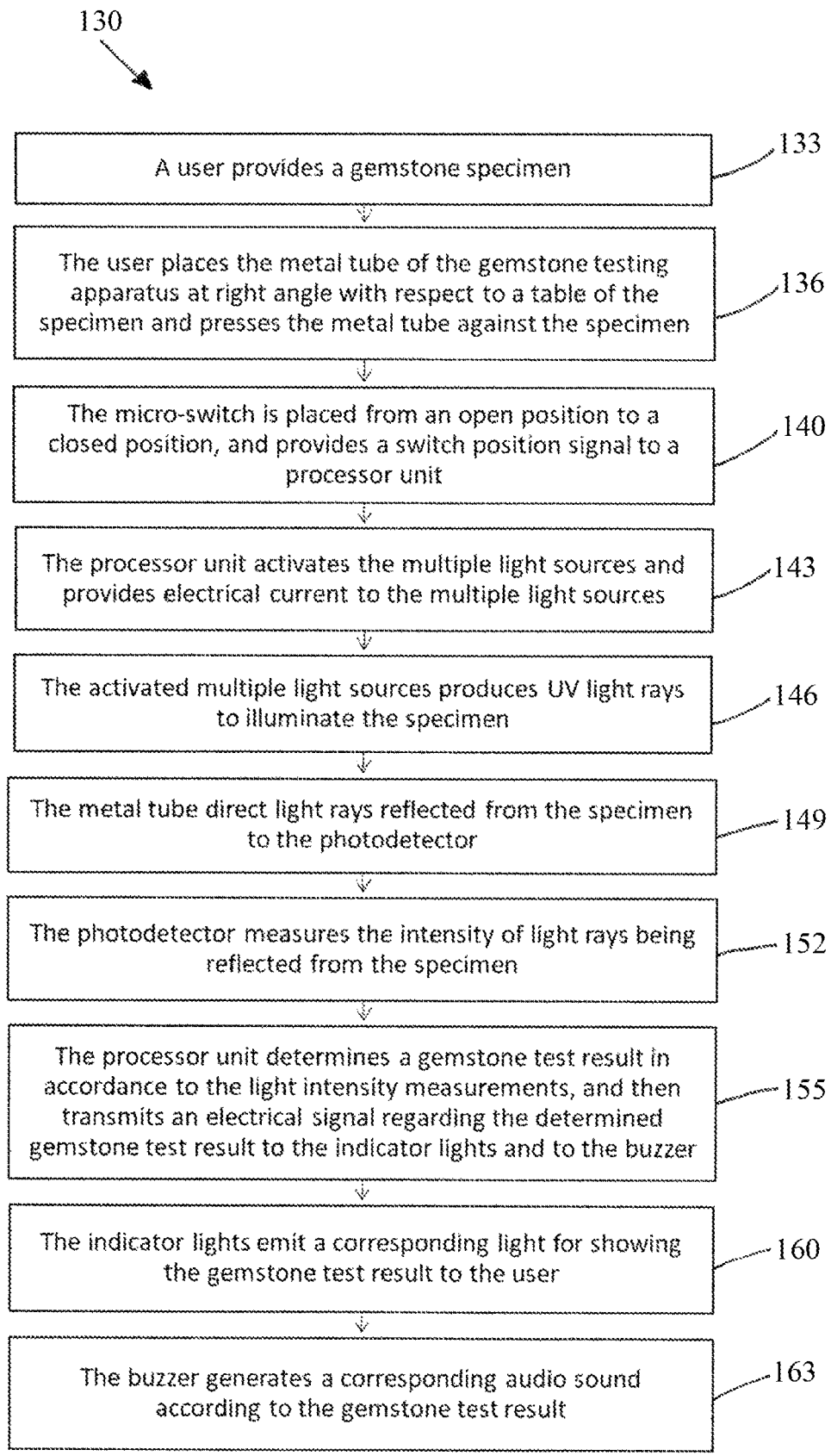
Figure 13:
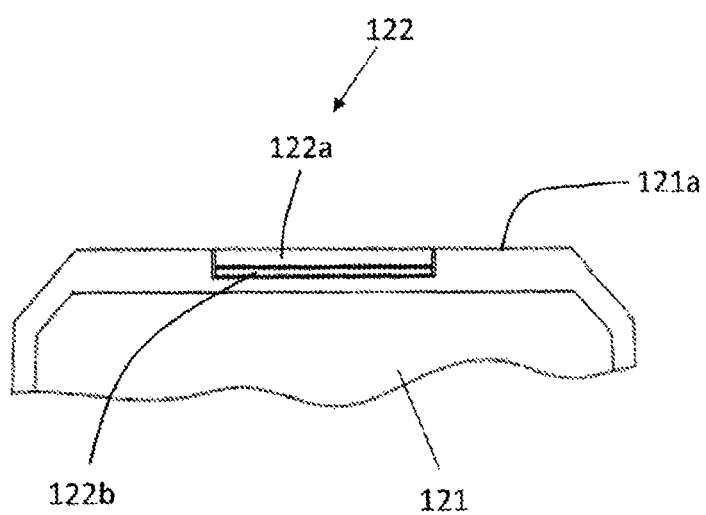
Figure 14:
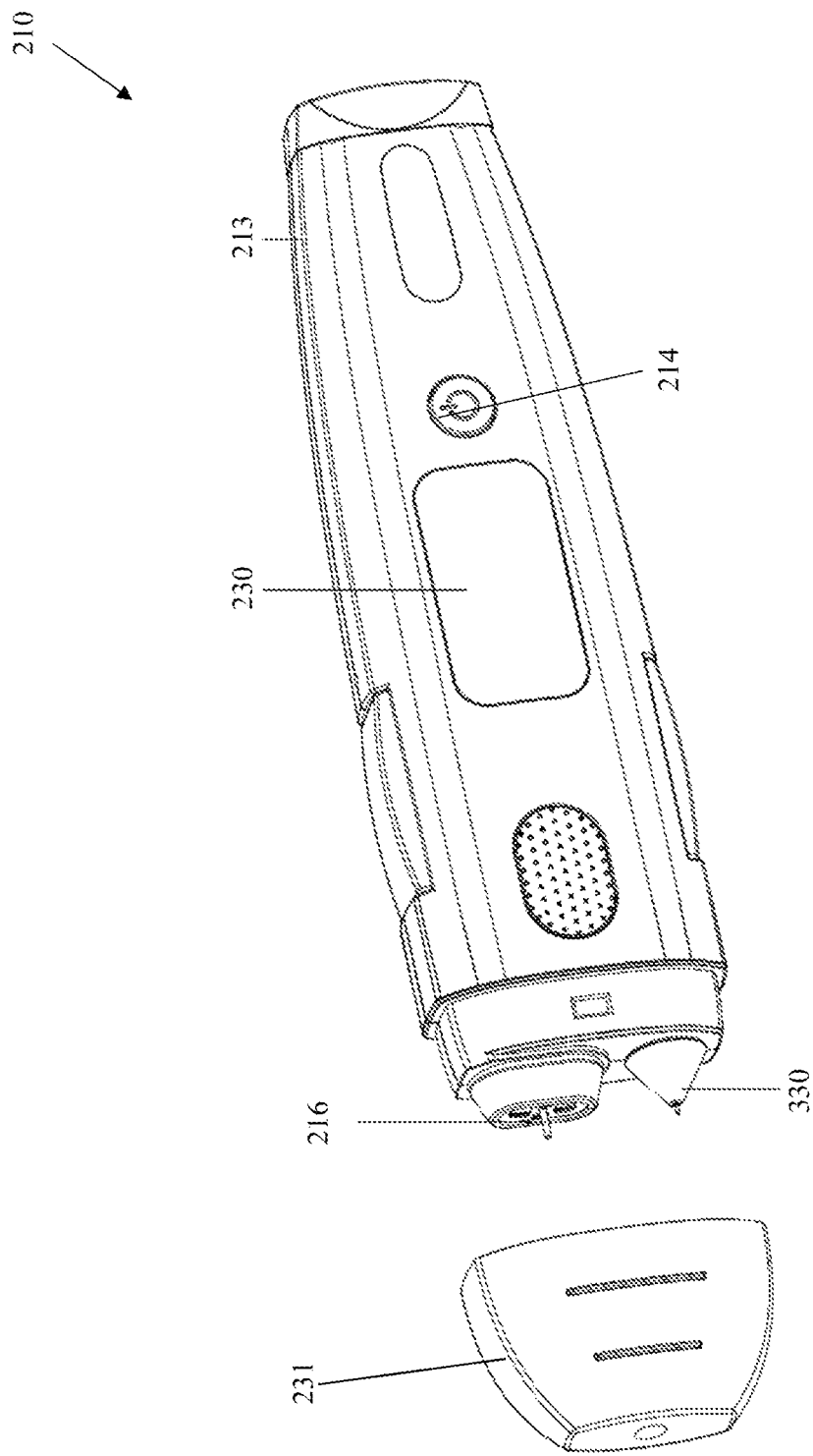
Figure 15:
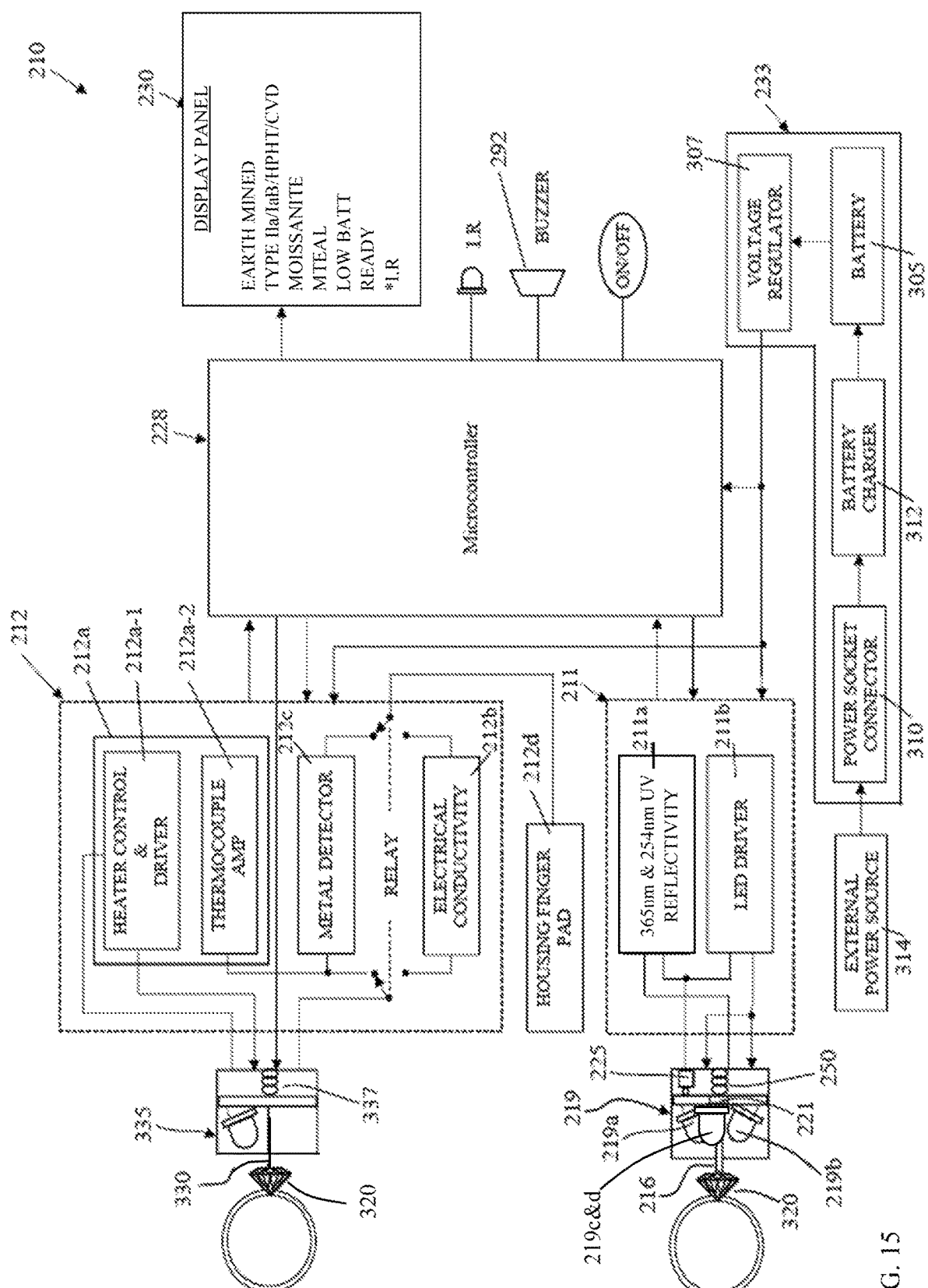
Figure 16:
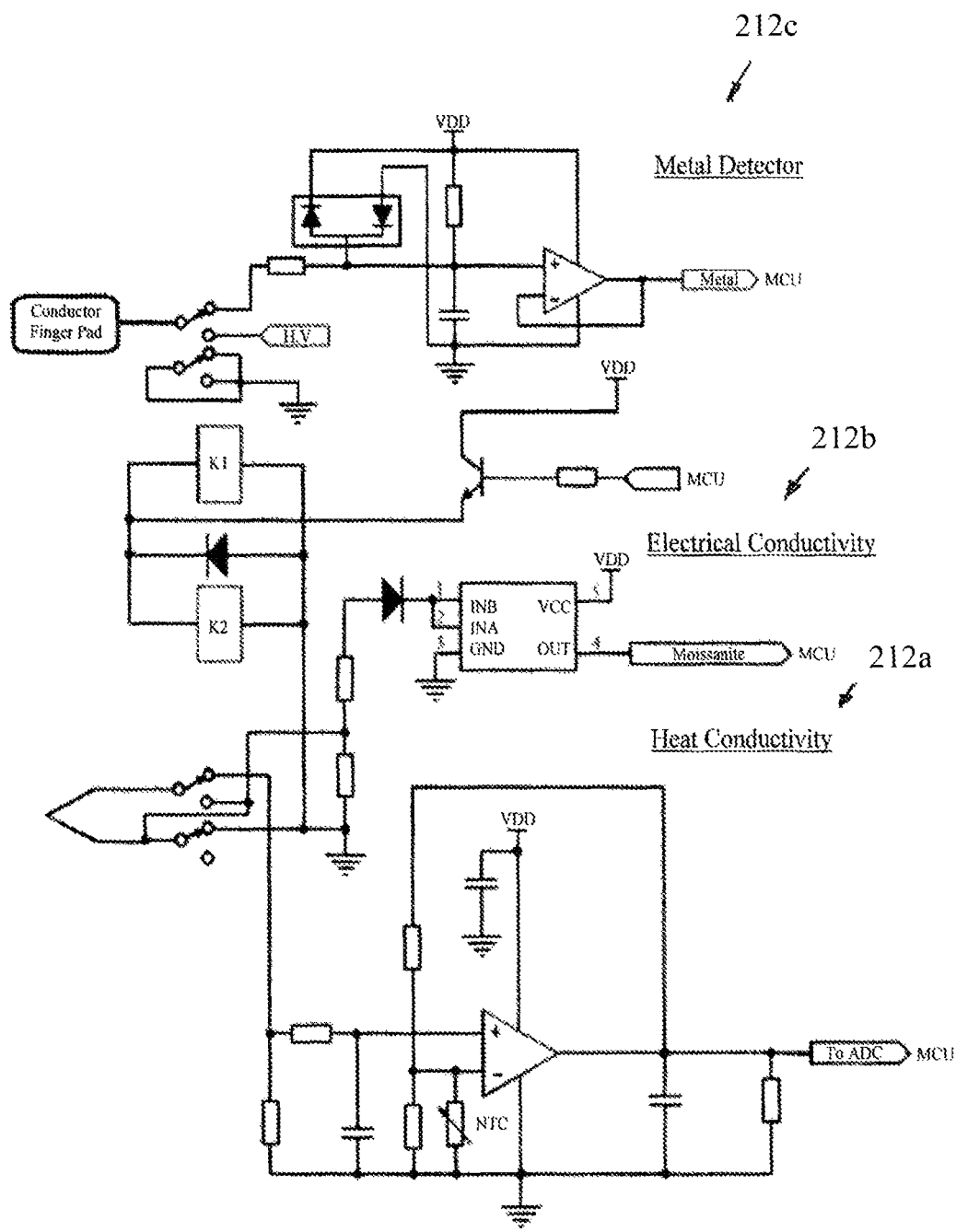
Figure 17:
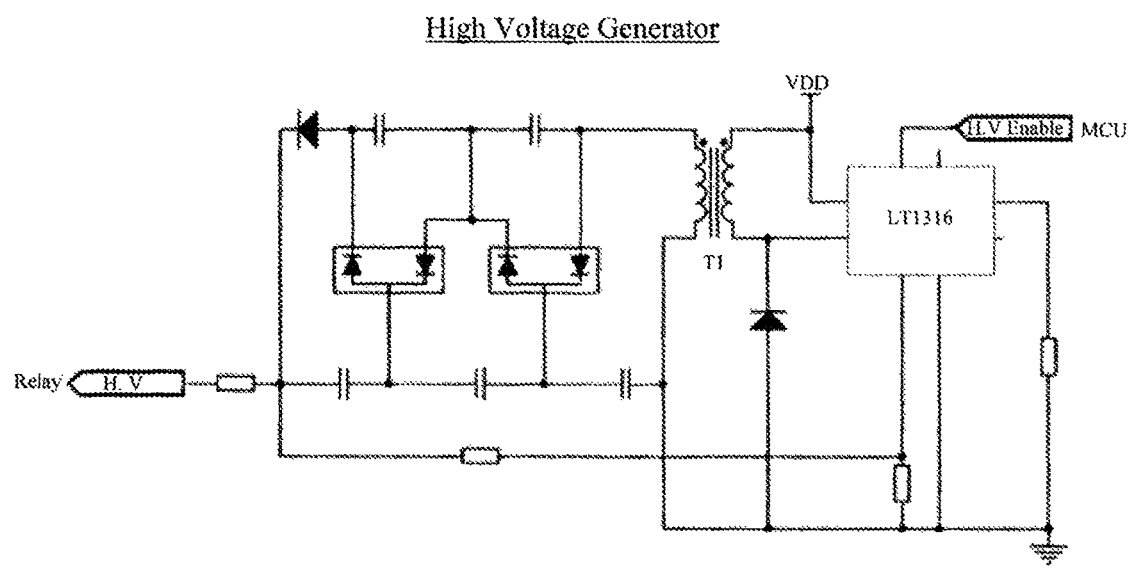
Figure 18:
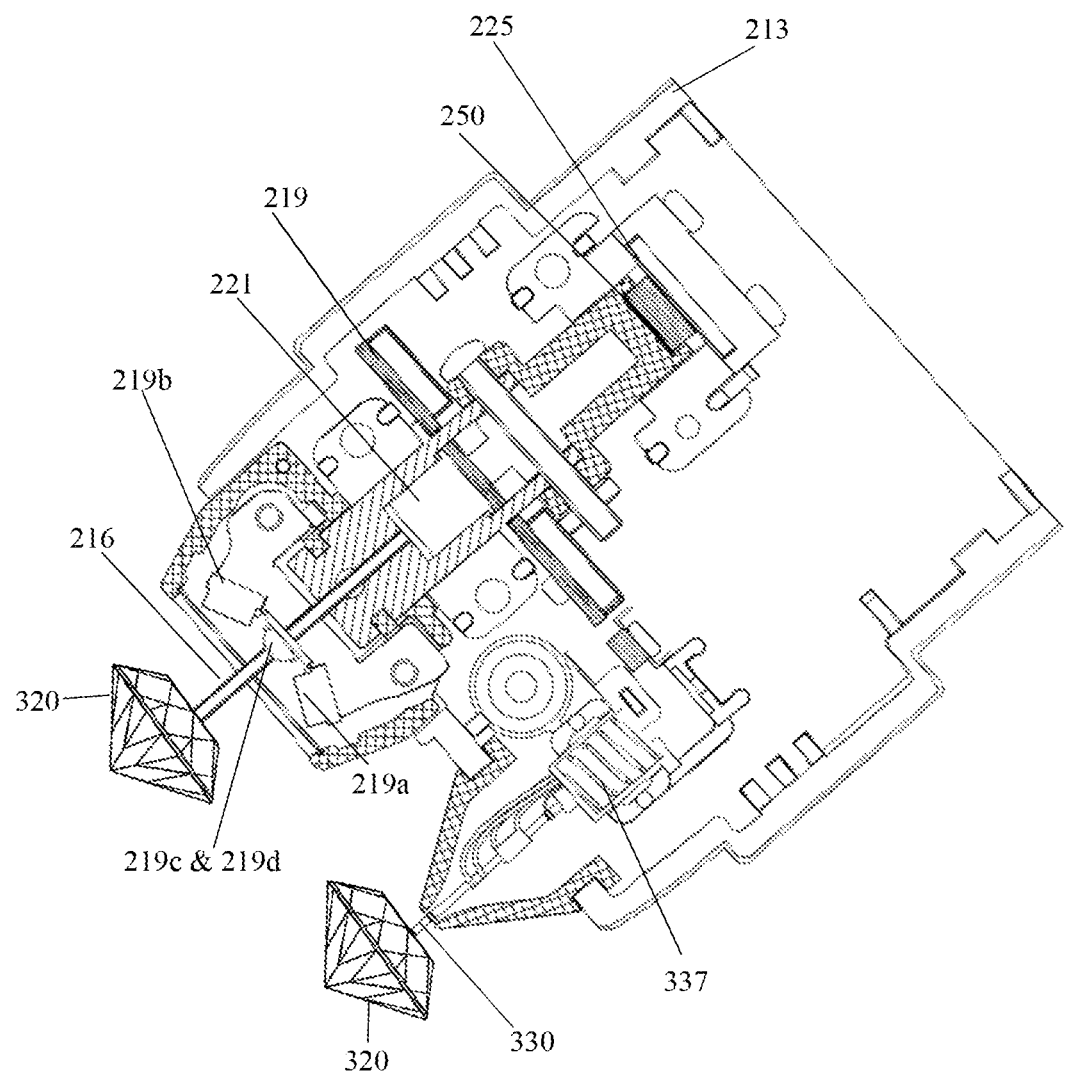
Figure 19:
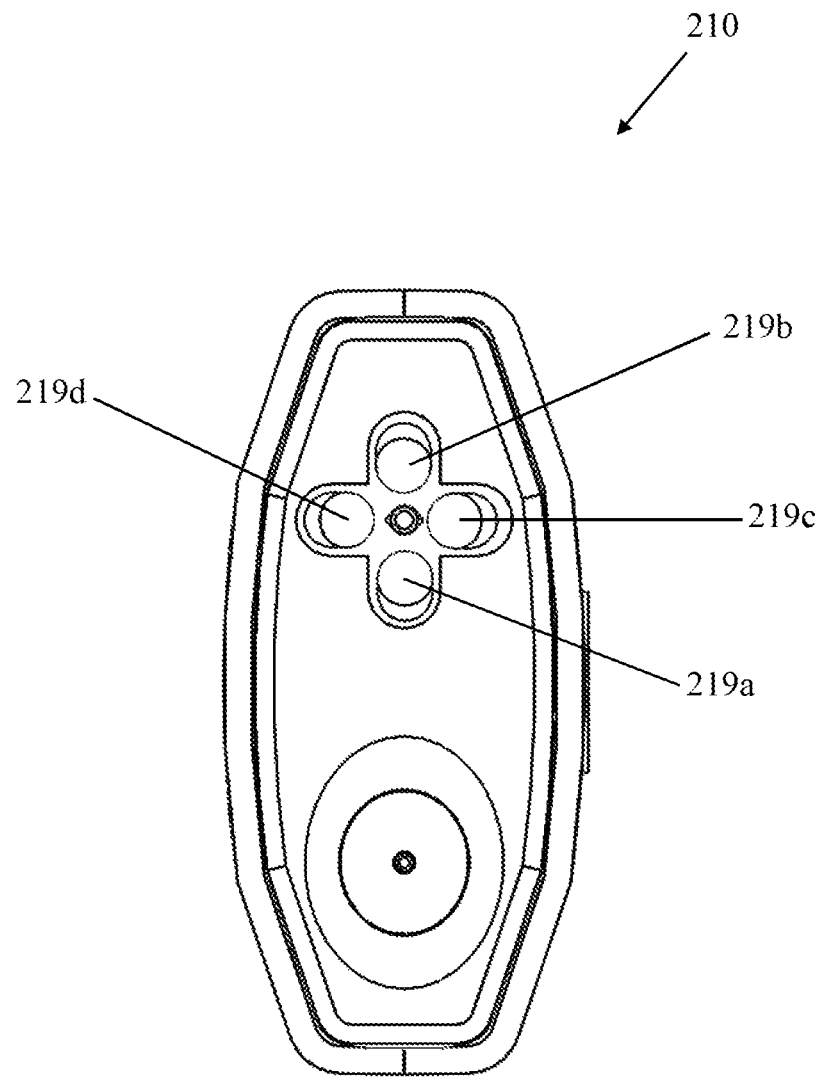
Figure 20:
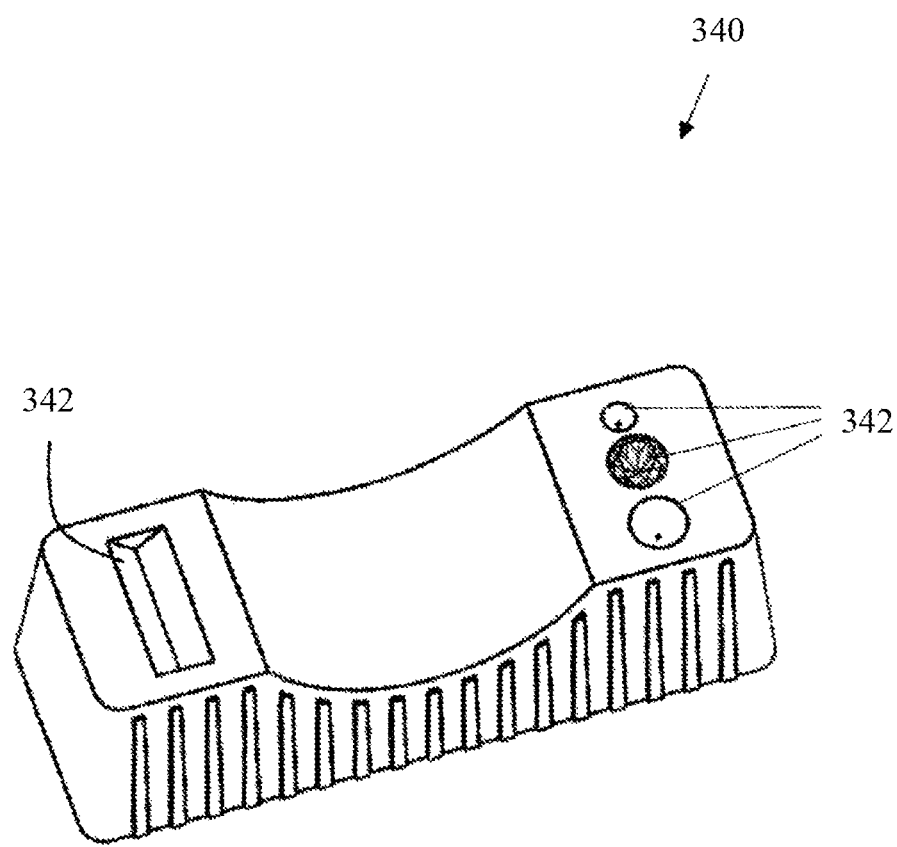
Figure 21:
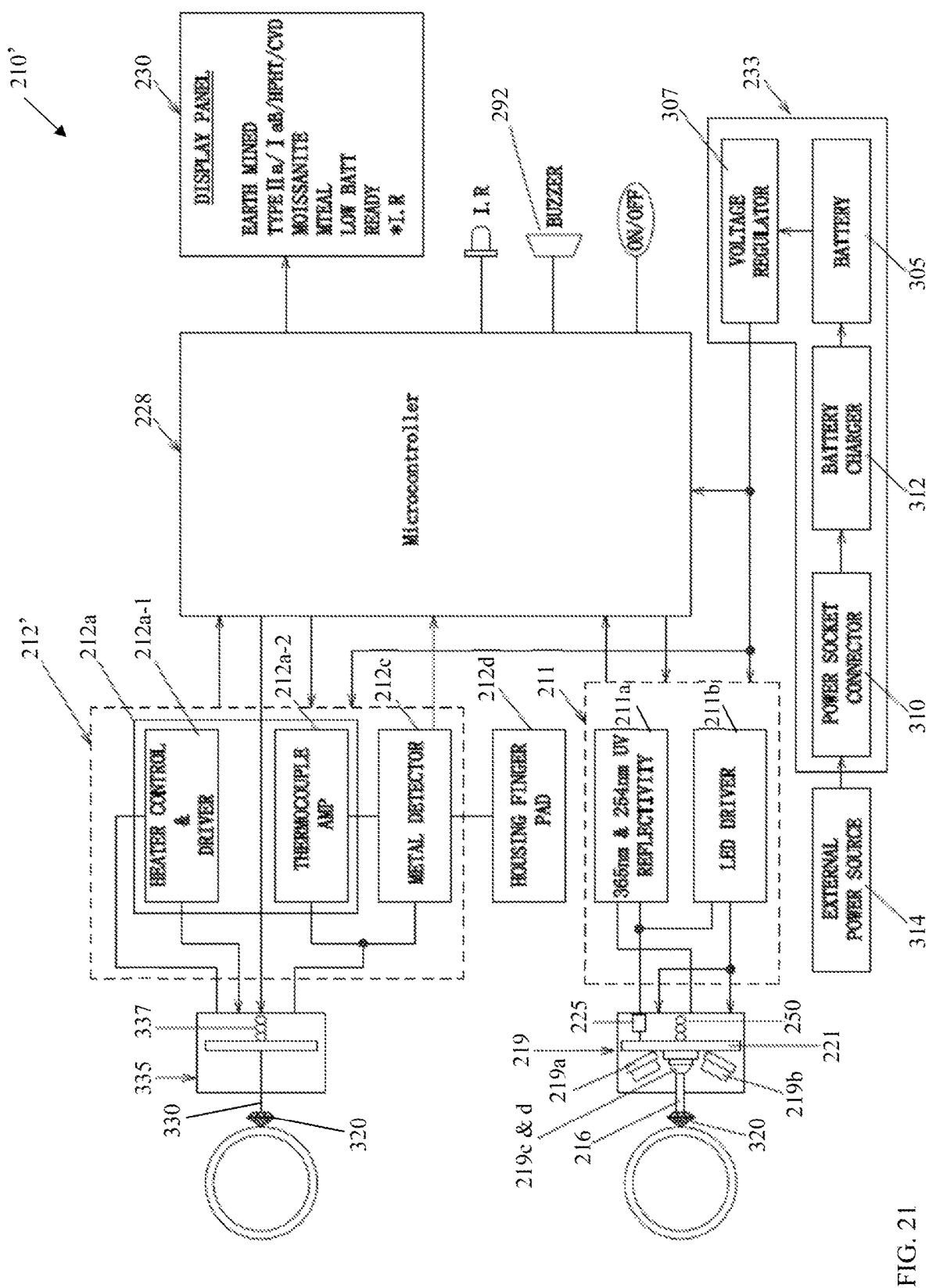

The subject matter of the application is described in greater detail in the accompanying Figures, in which FIG. 1 illustrates a perspective view of an improved light absorption gemstone testing apparatus, FIG. 2 illustrates a rear view of the light absorption gemstone testing apparatus of FIG. 1, FIG. 3 illustrates a partial cross-sectional view of a head portion of the light absorption gemstone testing apparatus of FIG. 1, FIG. 4 illustrates a partial cross-sectional view of the head portion of the light absorption gemstone testing apparatus of FIG. 1, FIG. 5 illustrates a front view of the head portion of the light absorption gemstone testing apparatus of FIG. 1, FIG. 6 illustrates an electronic block diagram of the light absorption gemstone testing apparatus of FIG. 1, FIG. 7 illustrates a simplified partial cross-sectional view of the head portion of the light absorption gemstone testing apparatus of FIG. 1, wherein a metal tube of the light absorption gemstone testing apparatus is placed at a centre portion of a table of a specimen, FIG. 8 illustrates a partial cross-sectional view of the head portion of the light absorption gemstone testing apparatus of FIG. 1, wherein the metal tube is placed at an edge of the table of the specimen, FIG. 9 illustrates a partial cross-sectional view of a head portion of another gemstone tester with a single light source, wherein a test probe of the gemstone tester is placed at a centre portion of the table of the specimen, FIG. 10 illustrates a partial cross-sectional view of the head portion of the light absorption gemstone testing apparatus of FIG. 9, wherein the test probe is placed at an edge of the table of the specimen, FIG. 11 illustrates a top view of an external cap with a gemstone test reference tablet for the light absorption gemstone testing apparatus of FIG. 1, FIG. 12 illustrates a flow chart of steps of a method of operating the light absorption gemstone testing apparatus of FIG. 1, FIG. 13 illustrates a partial side view of the gemstone test reference tablet of FIG. 11, FIG. 14 illustrates a first embodiment of a combination gemstone testing apparatus for testing a gemstone specimen, FIG. 15 illustrates an electronic block diagram of the combination gemstone testing apparatus of FIG. 14, FIG. 16 illustrates a metal detector circuit, an electrical conductivity test circuit, and a thermal conductivity test circuit of the block diagram of FIG. 15, FIG. 17 illustrates a voltage generator module of FIG. 16, FIG. 18 illustrates a test probe of a thermal and electrical conductivity test device of the combination gemstone testing apparatus of FIG. 15, FIG. 19 illustrates a front view of the combination gemstone testing apparatus of FIG. 14, FIG. 20 illustrates a stone rest for the gemstone specimen, and FIG. 21 illustrates an electronic block diagram of a second embodiment of the combination gemstone testing apparatus, which a variant of the combination gemstone testing apparatus of FIG. 14.

In the following description, details are provided to describe the embodiments of the specification. It shall be apparent to one skilled in the art, however, that the embodiments may be practised without such details.

Some parts of the embodiments have similar parts. The similar parts may have the same names or similar part numbers with an alphabet symbol or prime symbol. The description of one part applies by reference to another similar part, where appropriate, thereby reducing repetition of text without limiting the disclosure.

FIGS. 1 to 3 show an improved light absorption gemstone testing apparatus 10 to differentiate between a diamond and a moissanite gemstone. The gemstone testing apparatus 10 serves a light absorption test device.

In use, a gemstone specimen can be screened or tested using a thermal conductivity test. The thermal conductivity test is also called a heat conductivity test. If the thermal conductivity test indicates that the specimen could be a moissanite gemstone or a diamond gemstone, the light absorption gemstone testing apparatus 10 is then used to differentiate between the two.

Referring to FIGS. 1 and 6, the light absorption gemstone testing apparatus 10 comprises an elongated handheld casing 13 with a power on button 14, a test probe 16 with a light module 19 together with a photodetector 21, a pressure switch 25 that includes a mechanical micro-switch 52, an electronic testing unit 28, a display unit 30 together with a buzzer 92, and a power source unit 33. The photodetector 21 is also called an UV sensor.

The electronic testing unit 28, the buzzer 92, and the power source unit 33 are shown in FIG. 6 while the display unit 30 is shown in FIGS. 1 and 6.

The electronic testing unit 28 is also called an electronic testing circuit. The photodetector 21 is also called an ultraviolet (UV) sensor. The test probe 16 is also called a detector probe. The handheld casing 13 is also called an apparatus body. The power source unit 33 is also called a power source for the sake of brevity.

A part of the test probe 16, the light module 19, the photodetector 21, the pressure switch 25, the electronic testing unit 28, a part of the power source unit 33, and the buzzer 92 are placed inside the elongated handheld casing 13. The display unit 30 is placed on an outer surface of the elongated handheld casing 13. The electronic testing unit 28 is electrically connected to the power source unit 33, to the light module 19, to the photodetector 21, to the pressure switch 25, to the display unit 30, and to the buzzer 92. The electronic testing unit 28 is soldered on and is attached to a printed circuit board (PCB).

The handheld casing 13 includes an elongated hollow body portion 36, a head portion 38, and a spring support unit 40, as shown in FIGS. 1 and 3.

The elongated hollow body portion 36 essentially has a shape of a cylinder. The elongated hollow body portion 36 has a first end 36a and a second end 36b, which is positioned opposite to the first end 36a. The head portion 38 is positioned next to the first end 36a of the elongated hollow body portion 36. A longitudinal axis of the elongated hollow body portion 36 is aligned with a longitudinal axis of the head portion 38. The spring support unit 40 is placed inside the elongated hollow body portion 36 and is attached to the head portion 38.

As seen in FIGS. 1, 3, 7, and 8, the head portion 38 includes a hollow conical member 42 with an actuator member 44 and a support member 47. The actuator member 44 is integrally connected to the hollow conical member 42. The hollow conical member 42 is placed next to the first end 36a of the hollow body portion 36 of the handheld casing 13. The actuator member 44 and the support member 47 are placed inside the first end 36a of the hollow body portion 36. The actuator member 44 is movably connected to the support member 47. The support member 47 is fixed to the hollow body portion 36 of the handheld casing 13.

As seen in FIG. 3, the spring support unit 40 includes a plurality of coil torsion springs 50. Parts of the actuator member 44 are inserted into the coil torsion springs 50. The coil torsion springs 50 are adapted for pushing the support member 47 away from the hollow conical member 42.

The micro-switch 52 of the pressure switch 25 includes a rectangular body 55, an offset lever 57, and a single throw and single pole (STSP) switch 59, three electrical terminals 62. The STSP switch 59 includes an on/off button 65. One end of the offset lever 57 is movably attached to the rectangular body 55. A middle portion 57a of the offset lever 57 is placed next to the on/off button 65. Two ends of the STSP switch 59 are electrically connected to two of the electrical terminals 62. The offset lever 57 is placed adjacent to one end of the actuator member 44. The electrical terminals 62 are electrically connected to the electronic testing unit 28.

The test probe 16 includes a metal tube 68 together with a protective shell 74. The metal tube 68 is inserted in the protective shell 74.

In one example, the metal tube 68 has an inner surface that serves as a reflective surface 70. In another example, the metal tube 68 encloses an optical fibre, which is inserted inside the metal 68. The optical fibre provides a reflective surface 70.

The optical fibre refers to a flexible, transparent fibre or strand, which is made of glass or plastic. The strand has a very small diameter and it has two ends which allow transmission of light rays between the two ends. The diameter of the optical fibre is often slightly larger than a diameter of a human hair.

The optical fibre having a small diameter allows the metal tube 68 to be designed with also a small diameter. This small-diameter metal tube 68, which is intended for contacting a gemstone specimen, can then be used for touching small and large gemstone specimens. Such metal tube 68 is different from a probe tip with large diameter that is not suitable for touching a small specimen.

A first end 68a of the metal tube 68 protrudes from the head portion 38 and is placed outside the head portion 38. The protective shell 74 surrounds a second end 68b of the metal tube 68, and it touches the second end 68b of the metal tube 68.

The protective shell 74 also provides a cavity 76 that is placed next to the second end 68b of the metal tube 68.

The light module 19 includes two light sources 78 and two light sources 80, as illustrated in FIGS. 4 and 5. For the sake of simplicity, FIGS. 3, 7, and 8 do not show the light sources 80.

The light sources 78 and 80 are positioned near the test probe 16, and they are also placed around the test probe 16 in a symmetrical manner, as illustrated in FIG. 5. The light sources 78 are placed opposite to each other while the light sources 80 are placed opposite to each other. Each light source 78 and 80 includes a cylindrical body and a semi-spherical part that is placed at one end of the cylindrical body.

The cylindrical body is inclined at an angle of about 40 degrees with respect to the longitudinal axis of the metal tube 68, and it is pointing towards a predetermined location that is positioned near the first end 68a of the metal tube 68.

A transparent cover 81 is placed between the light sources 78 and 80 and the first end 68a of the metal tube 68. The transparent cover 81, the light sources 78, and the first end 68a are shown in FIG. 7. The light sources 80 is shown in FIGS. 5 and 6. For the sake of simplicity, the cover 81 is not shown in FIGS. 3, 4, 8. 9, and 10.

Referring to FIG. 6, the light sources 78 and 80 are electrically connected to the electronic testing unit 102 via current limiting resistors 96. Each light source 78 and 80 includes one ultraviolet (UV) Light Emitting Diode (LED).

As shown in FIG. 3, the photodetector 21 comprises a photodiode 84. The photodiode 84 is placed adjacent to the second end 68b of the metal tube 68, and it is placed inside the cavity 76 that is formed by the protective shell 74. The photodiode 84 is also positioned along a longitudinal axis of the metal tube 68. The size of the photodiode 84 is comparable with the size of a diameter of the second end 68b of the metal tube 68.

The photodetector 21 has a peak detection sensitivity that corresponds with the wavelength of the ultraviolet light rays from the light sources 78. The photodetector 21 is also electrically connected to the electronic testing unit 28.

The chamber that is formed by the protective shell 74 acts to allow only the reflected light rays from the metal tube 68 to reach the photodetector 21 while preventing other light rays from reaching the photodetector 21.

The display unit 30 comprises multiple indicator lights 89 together with a low battery indicator 108. The indicator lights 89 and the low battery indicator 108 are disposed on an outer surface of the hollow body portion 36 of the handheld casing 13. The display unit 30 is electrically connected to the electronic testing unit 28.

The buzzer 92 is placed inside the hollow body portion 36 of the handheld casing 13. The buzzer 92 is also electrically connected to the electronic testing unit 28.

As shown in FIG. 6, the electronic testing unit 28 includes a processor unit 102. The photodetector 21 and the light sources 78 and 80 together with the indicator lights 89, the low battery indicator 108, and the buzzer 92 of the display unit 30 are electrically connected to the processor unit 102.

The power source unit 33 comprises a battery module 105 with a voltage regulator 107, a power socket connector 110, and a battery charger 112. The battery module 105, and the voltage regulator 107 are placed inside the hollow body portion 36. The power socket connector 110 is partially enclosed in the hollow body portion 36 and is placed at the second end 36b of the hollow body portion 36. The battery charger 112 is adapted for electrically connecting to an external power source 114 and for electrically connecting to the power socket connector 110. The power socket connector 110 is electrically connected to the battery module 105. The battery module 105 and the voltage regulator 107 are adapted for providing electrical power to electronic components of the electronic testing unit 28. The battery module 105 includes a lithium battery that is electrically connected to contact terminals that are soldered onto the printed circuit board, which is attached to the electronic testing unit 28.

In one implementation, the metal tube 68 has a length of about 9.30 millimetre (mm), although the metal tube 68 can also be provided with other dimensions.

The light source 78 produces a UV light ray with a wavelength of about 365 nm while the light source 80 produces a UV light ray with a wavelength of about 254 nm. The photodetector 21 has a detection sensitivity that is suitable for detecting these light rays.

The indicator lights 89 may be provided by LEDs or LCDs (Liquid-Crystal Display) with suitably chosen colours.

Functionally, the light absorption gemstone testing apparatus 10 provides a way to differentiate between a colourless or near colourless diamond and a moissanite gemstone.

The colourless diamonds and the near colourless diamonds are defined according to the diamond colour chart, which is published by the Gemological Institute of America (GIA).

In use, a thermal conductivity test can be used to separate diamond and moissanite gemstones from simulants. Thereafter, the light absorption gemstone testing apparatus 10 can be used to differentiate between a diamond and a moissanite gemstone.

The light absorption gemstone testing apparatus 10 is intended to be held by a user such that the first end 68a of the metal tube 68 is placed on the surface of a specimen.

The user then presses the metal tube 68 against the specimen.

The hollow conical member 42 with the actuator member 44 then moves into the body portion 36, along the longitudinal axis of the elongated body portion 36 by a substantially small distance. The hollow conical member 42 with the actuator member 44 also move towards the micro-switch 52. This movement acts to compress the springs 50.

The actuator member 44 later pushes the offset lever 57 of the micro-switch 52 such that the offset lever 57 pushes the on/off button 65 of the micro-switch 52 into the rectangular body 55 of the micro-switch 52.

The micro-switch 52 can be placed in a closed and a normally open position. The above pushing of the on/off button 65 acts to place the micro-switch 52, from the open position to the closed position. The micro-switch 52 also acts to provide a switch position signal to the processor unit 102.

The current limiting resistor 96 acts to regulate electrical current to the light sources 78 and 80, when the light sources 78 and 80 are activated by the processor unit 102.

The activated light sources 78 produce ultraviolet light rays with a wavelength of about 365 nm to differentiate between a diamond gemstone that is colourless or near colourless and a moissanite gemstone.

The ultraviolet light rays are intended for illuminating a specimen that is placed near the test probe 16 when it is activated by the processor unit 102. The light ray is also called light for the sake of brevity.

The ultraviolet light rays have a predetermined fixed wavelength that is within a predetermined UV light spectrum band.

The ultraviolet light rays can also have different wavelengths that are within a predetermined range of the predetermined UV light spectrum band.

As seen in FIGS. 7 and 8, the arrangement of the two light sources 78 allow a table 120*a* of the specimen 120 to receive light rays from either one or two of the light sources 78, when the metal tube 68 is placed at different parts of the table 120*a*, such as an edge of the table 120*a*.

In practice, the size of the metal tube 68 is often smaller than the size of the table 120*a* of the specimen 120. Because of this, a user may place the metal tube 68 at different parts of the table 120*a* of the specimen 120. The metal tube 68 can be placed near a centre position or an edge of the table.

The table 120*a* of the specimen 120 refers to a facet or a flat side of the gemstone specimen 120, the facet being located at the top of the specimen. One example of the specimen 120 is a diamond or moissanite. The flat facet is usually the largest facet of the specimen 120.

When the metal tube 68 is placed substantially near or at the centre location of the table 120*a* of the specimen 120, the table 120*a* of the specimen 120 will receive light emitted from both light sources 78, as illustrated in FIG. 7.

When the metal tube 68 is not placed substantially near the centre location of the table 120*a* of the specimen 120, such as the edge of the specimen 120, the table 120*a* of the specimen 120 will still receive light emitted from one of the two light sources 78. This illustrated by ray lights with borders 78' in FIG. 8.

In short, the two light sources allow the table 120*a* of the specimen 120 to receive light rays from the light sources even when the metal tube 68 is placed at different parts of the table 120*a* of the specimen 120.

This is different from other gemstone testers in which the tester includes a test probe tube and just one single light source.

When the test probe tube is placed near or at a centre location of a table 120*a* of a specimen 120, the table 120*a* will receive light rays from the single light source, as shown in FIG. 9.

When the probe tube is placed at an edge of the table 120*a* of the specimen 120, only a side facet 120*b* of the specimen 120 may receive light rays from the single light source, as shown in FIG. 10. In other words, no light rays or little light rays are directed onto the table 120*a* of the specimen.

The specimen 120 may then not receive enough light rays for testing the specimen 120. This then degrades or affects the testing to the specimen 120.

Referring to the specimen 120, the heat conductivity test has already indicated that the specimen 120 belongs to a category of either a moissanite gemstone or a diamond gemstone. In other words, the specimen 120 can be a moissanite gemstone or a diamond gemstone.

If the specimen 120 is a moissanite gemstone, the moissanite gemstone will absorb these light rays from the light sources 78, which have a wavelength of about 365 nm. In other words, no or little light rays are reflected from the moissanite gemstone. If the specimen 120 is a colourless or near colourless diamond gemstone, the diamond gemstone will reflect the light rays or reflect a significant part of the light rays from the light sources 78.

The metal tube 68 acts as a light guide to receive the light rays reflected from the specimen 120. In detail, the second end 68*b* of the metal tube 68 receives the light rays reflected from the specimen 120. The inner surface of the metal tube 68 then reflects these light rays without absorbing these light rays. The inner surface also directs these light rays to the second end 68*b* of the metal tube 68 and towards the photodetector 21.

The transparent cover 81 allows light rays that originate from the light sources 78 and 80 reach an area next to the first end 68*a* of the metal tube 68. In use, the specimen is placed in this area.

Referring to the protective shell 74, it provides structural support for the two light sources 78 and 80 and for the metal tube 68, preventing them from moving.

The photodetector 21 detects and measures the intensity of light rays being reflected from the specimen. The photodetector 21 then sends the light measurements to the processor unit 102.

The indicator lights 89 receive an electrical signal regarding a gemstone test result from the processor unit 102 and then emits a corresponding light ray for showing the gemstone test result to a user.

As another example, a first LED (Light Emitting Diode) of the indicator lights 89 is activated for showing that the gemstone testing apparatus 10 detects diamond. A second LED of the indicator lights 89 is activated for showing that the gemstone testing apparatus 10 detects moissanite.

The buzzer 92 also receives a signal from the processor unit 102 and generates a corresponding audio sound in accordance with the signal. The buzzer 92 produces a continuous beeping sound when the gemstone testing apparatus 10 detects a diamond. The buzzer 92 produces a short intermittent beeping sound when the gemstone testing apparatus 10 detects moissanite.

After the indicator lights 89 emit a light ray for showing the gemstone test result to the user, the user can remove the metal tube 68 away from the specimen 120.

The coil torsion springs 50, as shown in FIG. 3, then pushes the hollow conical member 42 and the actuator member 44 away from the micro-switch 52.

The actuator member 44 then does not push and does not contact the offset lever 57 of the micro-switch 52.

The micro-switch 52 then returns to its open position from its closed position. The micro-switch 52 then provides a switch position signal to the processor unit 102.

When the micro-switch 52 is placed in the closed position, the processor unit 102 activates the battery module 105 to supply electrical power to the light sources 78, to the electronic testing unit 28, and to the display unit 30.

The voltage regulator 107 allows the battery module 105 to provide an output voltage with a constant voltage level.

The battery charger 112 together with the power socket connector 110 is used for connecting to an external power source 114. The connecting allows the external power source 114 to charge the battery module 105. The charging provides electrical energy to the battery module 105.

The processor unit 102 includes a program or instructions to receive a switch position signal from the micro-switch 52. After this, the processor unit 102 activates the light sources 78 or 80 according to the received switch position signal. The processor unit 102 later also receives light intensity measurements from the photodetector 21 after a predetermined period. The processor unit 102 then determines a gemstone test result in accordance with the light intensity measurements.

The processor unit 102 transmits an electrical signal regarding the determined gemstone test result to the indicator lights 89. The processor unit 102 can also send a corresponding signal to the buzzer 92.

The processor unit 102 monitors the output voltage of the battery module 105 and provides an alert signal to the low battery indicator 108. The low battery indicator 108 then emits a corresponding light ray to the user.

The handheld casing 13 acts to contain and protect parts of the gemstone testing apparatus, including the light module 19, the test probe 16, the power source unit 33 and the electronic testing unit 28 and the display unit 30.

The hollow conical member 42 of the head portion 38 is used for containing and protecting the light sources 78, the test probe 16, and the photodetector 21. The hollow conical member 42 also enclosed a part of the printed circuit board, which is attached to electronic testing unit 28.

The elongated hollow body portion 36 is provided for containing and protecting the pressure switch, the display unit 30, the power source unit 33 and a part of the electronic testing unit 28.

The light absorption gemstone testing apparatus 10 provides several benefits.

The two light sources 78 and 80 enable the table 120a of the specimen 120 to receive sufficient light rays from the light sources 78 and 80, even when the metal tube 68 is placed at different parts of the table 120a, such as an edge of the table 120a.

In use, the specimen 120 is often small. Because of this, a user may place the metal tube 68 at different parts of the table 120a of the specimen 120. For example, the metal tube 68 can be placed near a centre location of the table 120a of the specimen 120. It can also be placed at an edge of the table 120a. Despite this, the two light sources 78 or 80 enable the specimen 120 to receive enough light rays for testing the specimen.

The length of the metal tube 68 can also prevent the metal tube 68 from being easily bent. A distance between the first end 68a of the metal tube 68 and the light sources 78 is also short enough to enable light rays from the light sources 78 to reach the specimen 120 with no or little loss of light rays, thereby not reducing light intensity.

In a general sense, the indicator lights 89 can be replaced by a display panel, such as a colour or a monochrome screen display, which can be provided by a Liquid Crystal Display (LCD) or an Organic Light-Emitting Diode (OLED) display.

The handheld casing 13 can comprise a catch which allows an external cap 121 to be attached to the handheld casing 13 using a snap-fit mechanism. The external cap 121 is used for protecting the test probe 16 from being damaged.

As shown in FIGS. 11 and 13, the external cap 121 can include a fool-proof test disc 122.

In a general sense, the external cap 121 can be provided with or without the test disc 122.

The test disc 122 is also called a gemstone test reference tablet. The term "fool-proof" implies that the test disc 122 is simple and easy to use such that a user does not or seldom misuses the test disc 122.

The test disc 122 is provided on an outer surface 121a of the external cap 121 for easy access. In particular, the outer surface 121a of the external cap 121 has a recessed area, wherein the test disc 122 is placed on the recessed area.

The test disc 122 includes a layer 122a of transparent material and a layer 122b of reflective material. An inner surface of the transparent material layer 122a is placed over and next to an outer surface of the reflective material layer 122b such that the transparent material layer 122a protects the reflective material layer 122b from being scratched or cut. An inner surface of the reflective material layer 122b is placed next to the recessed area of the external cap 121.

A user may use the test disc 122 to check the functions of the gemstone testing apparatus 10. The user presses the first end 68a of the metal tube 68 of the test probe 16 of the gemstone testing apparatus 10 against the gemstone test reference tablet 122. The reflective material layer 122b then acts to reflect light rays from the light sources 78 or 80 of the gemstone testing apparatus 10, just like a diamond, while the transparent material layer 122a acts to protect the reflective material layer 122b.

The metal tube 68 can be replaced by a light guide, such as a hollow tube, wherein an inner surface of the hollow tube is coated with a reflective layer.

The light absorption gemstone testing apparatus 10 can include three or more light sources, instead of just two light sources. These light sources are placed around the metal tube 68 in a symmetric manner. Each of the light sources can be positioned at a predetermined angle with respect to the longitudinal axis of the gemstone testing apparatus 10. The multiple light sources can allow the production of light rays with a higher intensity for illuminating the specimen 120.

The light sources can be replaced by a ring light enclosing the test probe 16. The ring light can be configured to emit light rays that are directed to a location near the first end 68a of the metal tube 68. The ring light can also enable the production of light rays with a higher intensity for illuminating the specimen 120.

The processor unit 102 comprises a peripheral module that includes a timer. The timer can be programmed or instructed to switch off the electrical power of the gemstone testing apparatus 10 when the electronic testing unit 28 is inactive for a predetermined period. Put differently, the gemstone testing apparatus 10 is automatically powered off when it is not in use for a predetermined period to conserve or save power.

The display unit 30 can include an electrical power indicator for showing that the electronic testing unit 28 is powered or energized.

Although one method of operating the light absorption gemstone testing apparatus 10 is provided below, the gemstone testing apparatus 10 can also operate with other methods.

FIG. 12 shows a flow chart 130 of one method of operating the light absorption gemstone testing apparatus 10.

The flow chart 130 includes a process step 133 of a user providing a specimen 120.

The user then presses the metal tube 68 of the gemstone testing apparatus 10 against the specimen, in a process step 136. The metal tube 68 is placed such that it is about at right angle with respect to the table 120a of the specimen 120.

This later causes the micro-switch 52 to be placed, from its open position to the closed position, in a process step 140. The micro-switch 52 also provides a switch position signal to the processor unit 102.

The processor unit 102 activates the multiple light sources and provides electrical current to the multiple light sources 78 or 80, in a process step 143.

The activated multiple light sources 78 or 80 afterwards produces ultraviolet light rays to illuminate the specimen 120, in a process step 146.

The metal tube 68 subsequently directs these light rays to the second end 68b of the metal tube 68 and to the photodetector 21, in a process step 149.

The photodetector 21 then measures the intensity of light rays being reflected from the specimen 120, in a process step 152.

The processor unit 102 then determines a gemstone test result in accordance with the light intensity measurements. The processor unit 102 transmits an electrical signal regarding the determined gemstone test result to the indicator lights 89 and to the buzzer 92, in a process step 155.

The indicator lights 89 receive the electrical signal regarding a gemstone test result from the processor unit 102 and then emits a corresponding light ray for showing the gemstone test result to the user, in a process step 160.

The buzzer 92 also receives the electrical signal from the processor unit 102 and then produces a corresponding audio sound according to the gemstone test result, in a process step 163.

FIG. 14 shows another improved combination gemstone testing apparatus 210.

The combination gemstone testing apparatus 210 includes an elongated handheld casing 213 with an electrical test circuit and a display unit 230. The handheld casing 213 encloses the electrical test circuit. The handheld casing 213 is also called an apparatus body. The display unit 230 is attached to an external part of the handheld casing 213.

As seen in FIG. 15, the electrical test circuit includes a test probe 330, a thermal and electrical conductivity test unit 212, a light absorption electrical test unit 211 and supporting electronics. The handheld casing 213 surrounds and encloses the light absorption test unit 211, the thermal and electrical conductivity test unit 212, and the supporting electronics.

Although, in this example, the combination gemstone testing apparatus 210 is provided here with an electrical conductivity test unit, the combination gemstone testing apparatus 210 can also be provided without the electrical conductivity test unit.

As seen in FIG. 14, the handheld casing 213 includes an elongated hollow body portion and a head portion. The head portion is placed next to one end of the elongated hollow body portion.

As seen in FIG. 15, the supporting electronics includes an electronic testing unit 228, a buzzer 292, and a power source unit 233. The electronic testing unit 228, the display unit 230, and the buzzer 292 are electrically connected to the power source unit 233. Moreover, the light absorption test unit 211 and the thermal and electrical conductivity test unit 212 are also electrically connected to the power source unit 233.

Referring to the thermal and electrical conductivity test unit 212, it includes a test probe 330, a conductivity test module, and a conductive housing finger pad 212d. The conductivity test module is electrically connected to the test probe 330 and to the housing finger pad 212d.

The test probe 330 includes a copper rod or a thermocouple probe and a spring element 337. An outer end of the copper rod protrudes from the head portion of the handheld casing 213 while an inner end of the copper rod is placed in a hollow part of the head portion, as shown in FIG. 18. The inner end of the copper rod is connected to the spring element 337, as shown in FIG. 15.

The conductivity test module comprises a thermal conductivity test circuit module 212a, an electrical conductivity test circuit module 212b, and a metal detector circuit 212c. The metal detector circuit 212c is electrically connected to the housing finger pad 212d.

The thermal conductivity test circuit module 212a includes a heater control and driver circuit 212a-1, and a thermocouple amplifier circuit 212a-2. The heater control and driver circuit 212a-1 and the thermocouple amplifier circuit 212a-2 are electrically connected to the copper rod of the test probe 330 and to the electronic testing unit 228.

Referring to FIG. 15, the electrical conductivity test circuit module 212b includes an ultraviolet (UV) light module 335. The UV light module 335 is placed near the copper rod.

The electrical conductivity UV light module 335 includes a UV Light Emitting Diode (LED) that generates light rays with a wavelength of about 365 nm. This UV LED is provided inside a cylindrical reflector portion of the head portion of the handheld casing 213. The light ray is also called light for the sake of brevity.

In a general sense, the electrical conductivity UV light module 335 can be replaced by a visible violet light (VVL) light module. The UVL light module includes a Light Emitting Diode (LED) that generates light rays with a wavelength of about 425 nm. The light rays can have a wavelength of about 400 nm to about 430 nm with a peak light intensity of about 425 nm.

FIG. 16 shows electronic components of the thermal conductivity test circuit module 212a, electronic components of the electrical conductivity test circuit module 212b, and electronic components of the metal detector circuit 212c.

FIG. 17 shows several electronic components of a high voltage generator module of the electrical conductivity test circuit module 212b.

Referring to the light absorption test unit 211, it includes a test probe tube 216, an ultraviolet (UV) light module 219, and a photodetector 221, as seen in FIG. 15. The light absorption test unit 211 also includes an electronic test circuit, which is not shown in FIG. 15.

The photodetector 221 is also called an ultraviolet (UV) sensor. The test probe tube 216 is also called a detector probe. The light absorption UV light module 219 and the photodetector 221 are electrically connected to the electronic test circuit. The light absorption UV light module 219 is placed near the test probe tube 216.

The test probe tube 216 includes a straight metal tube with a reflective inner surface and a probe pressure-switch 225. An outer end of the metal tube protrudes from the head portion of the handheld casing 213 while an inner end of the metal tube is placed in a hollow part of the head portion. Moreover, the pressure-switch 225 includes a thin film pressure sensor. Electrical terminals of the thin film pressure sensor are electrically connected to the electronic testing unit 228. The thin film pressure sensor is placed next to the inner end of the metal tube. The probe pressure-switch 225 is shown in FIG. 18.

In a general sense, the thin film pressure sensor can be replaced by a mechanical micro-switch.

The light absorption UV light module 219 includes two light sources 219a and 219b as well as two light sources 219c and 219d.

Each light source 219a and 219b includes a first UV Light Emitting Diode (LED). The light sources 219a and 219b are positioned near the metal tube, and they are also placed opposite each other and are placed around the metal tube in a symmetrical manner.

Similarly, each light source 219c and 219d includes a second UV LED. The light sources 219c and 219d are positioned near the metal tube, and they are also placed opposite each other and are placed around the metal tube in a symmetrical manner, as shown in FIG. 19.

The photodetector 221 refers to a photodiode. The photodiode is placed in the hollow part of the casing head portion such that the photodiode is placed adjacent to the inner end of the metal tube. The photodiode is also positioned along a longitudinal axis of the metal tube. The photodiode is adapted to have a peak detection sensitivity that corresponds with a wavelength of light rays from the light sources 219a and 219b.

The light sources 219a and 219b produce a UV light ray with a wavelength of about 365 nm. Similarly, the light sources 219c and 219d produce a UV light ray with a wavelength of about 254 nm. The photodetector 221 has a detection sensitivity for detecting these light rays.

The electronic test circuit also includes a reflectivity electrical circuit 211a and an LED driver 211b. The LED driver 211b is electrically connected to the light sources 219a and 219b, to the light sources 219c and 219d, and to the electronic testing unit 228. The reflectivity electrical circuit 211a is electrically connected to the photodiode of the photodetector 221 and to the electronic testing unit 228.

Referring to the electronic testing unit 228, it includes a computing processor unit or a microcontroller.

Referring to the display unit 230, it comprises a Liquid Crystal Display (LCD) display panel. The display unit 230 is electrically connected to the electronic testing unit 228.

With reference to the buzzer 292, it is placed inside the handheld casing 213. The buzzer 292 is electrically connected to the electronic testing unit 228.

Referring to the power source unit 233, it comprises a power socket connector 310, a battery charger 312, and a battery module 305 with a voltage regulator 307. The battery module 305 includes a lithium battery. The battery charger 312, the battery module 305, and the voltage regulator 307 are placed inside the hollow body portion of the handheld casing 213. The power socket connector 310 is placed at the one end of the hollow body portion.

The power socket connector 310 is electrically connected to the battery charger 312. The battery charger 312 is electrically connected to the battery module 305.

The voltage regulator 307 is electrically connected to the UV light module 219, to the photodetector 221, and to the light absorption test unit 211. Furthermore, the voltage regulator 307 is electrically connected to the electrical conductivity UV light module 335, and the thermal and electrical conductivity test unit 212. Moreover, the voltage regulator 307 is connected electrically to the electronic testing unit 228, which is electrically connected to the display unit 230, and to the buzzer 292.

Further, the handheld casing 213 can comprise a catch for allowing the handheld casing 213 to attach to an external cap 231 using a snap-fit mechanism. The external cap 231 is illustrated in FIG. 14. The external cap 231 is similar to the external cap 121 that is described above.

The external cap 231 can be attached to and can be detached from the handheld casing 213. The external cap 231 is used for protecting the test probe tube 216 and the test probe 330 from being damaged.

The external cap 231 can include a fool-proof test disc. The test disc is also called a gemstone test reference tablet.

The test disc is provided on an outer surface of the external cap 231 for easy access. In particular, the outer surface of the external cap 231 has a recessed area, wherein the test disc is placed on the recessed area.

The test disc includes a layer of transparent material and a layer of reflective material. An inner surface of the transparent material layer is placed over and next to an outer surface of the reflective material layer such that the transparent material layer protects the reflective material layer from being scratched or cut. An inner surface of the reflective material layer is placed next to the recessed area of the external cap 231.

A user may use the test disc to check the functions of the combination gemstone testing apparatus 210. The user presses one end of the metal tube of the test probe 216 of the gemstone testing apparatus 210 against the gemstone test reference tablet. The reflective material layer then acts to reflect light rays from the light absorption UV light module 219 of the gemstone testing apparatus 210, just like a diamond, while the transparent material layer acts to protect the reflective material layer.

Functionally, the thermal conductivity test circuit module 212a provides a method to separate simulant, such as cubic zirconia and sapphire or glass from a group consisting of diamond and moissanite.

This method uses a thermal conductivity test, and it is described below.

The method includes a process step of a user pressing a power on button 214 on the casing 213 to activate the heater control and driver circuit 212a-1 for providing heat to the test probe 330. The power on button 214 is illustrated in FIG. 14.

The thermocouple amplifier circuit 212a-2 later measures temperature of the test probe 330 and sends the respective measurement to the processor unit of the electronic testing unit 228.

When the temperature measurement reaches a predetermined desired temperature, the processor unit then controls or adjusts the heater control and driver circuit 212a-1 such that the temperature measurement is maintained at the predetermined desired temperature.

The user then holds and positions a gemstone specimen 320 near or next to the gemstone test apparatus 210.

Especially for a gemstone specimen 320 that is provided as in the form of a loose stone, the user may place the gemstone specimen 320 on a stone rest or holder while the user holds the stone rest.

FIG. 20 shows a stone rest 340 for the gemstone specimen 320.

The stone rest 340 comprises different recessed areas 342 that are configured for receiving different gemstones with different dimensions. The recessed areas 342 positions and holds the gemstone specimen 320 such that the gemstone specimen 320 is stable for testing.

Alternatively, especially for a gemstone specimen 320 is provided a stone for mounting, the user may mount the gemstone specimen 320 on a ring and then the user hold or wear the ring on his finger, wherein the user positions and holds the gemstone specimen 320 such that the gemstone specimen 320 is stable for testing.

The test probe 330 is then placed on a table or a major top surface of the specimen 320.

The spring element 337 enables the test probe 330 to provide consistent pressure essentially on the gemstone specimen 320.

The spring element 337 also acts to prevent the test probe 330 from being bent.

The placing of the test probe 330 onto the specimen 320 also acts to press the test probe 330 against the specimen 320. The spring element 337 then allows the test probe 330 to move slightly inwards. This inward movement serves to prevent the test probe 330 from being bent during this pressing. After this, when the test probe 330 is not pressed against the specimen 320, the spring element 337 acts to move the test probe 330 to its initial position.

The test probe 330, which is placed on the table of the specimen 320, then transmits this heat to the table of the specimen 320.

The thermocouple amplifier circuit 212a-2 later measures heat dissipation rate of the test probe 330 and sends the respective measurement to the processor unit of the electronic testing unit 228.

Moissanite and diamond have comparable thermal conductivities. In comparison, simulant, such as cubic zirconia and sapphire, can be distinguished from a group consisting of diamond and moissanite by comparing their thermal conductivity properties.

The processor unit afterwards determines or selects a category of the specimen 320 according to the heat dissipation measurements. The processor unit determines whether the specimen 320 falls under the category of simulant or under the category of the group consisting of diamond and moissanite.

The processor unit then sends a signal to the display unit 230 for showing or indicating the determined category to a user.

The display unit 230 can provide a message for the user regarding proceeding for further testing of diamonds.

If the processor unit determines that the specimen 320 falls under the category of the group consisting of diamond and moissanite, the display unit 230 then provides a message to the user to proceed for further gemstone testing.

As a precaution, the metal detector circuit 212c automatically detects any accidentally touching of a metal surface by the test probe 330.

When the metal detector circuit 212c detects this touching, the processor unit generates a corresponding acoustic, optic, or acoustic and optic alert signal to indicate this touching to the user.

Functionally, the electrical conductivity test circuit module 212b provides a method to differentiate between colourless or near colourless diamonds and most moissanite gemstones.

In some implementations, this method is not performed.

The method uses an electrical conductivity test, and it is described below.

The electrical conductivity test can be done automatically after the thermal conductivity test. The processor unit automatically initiates the electrical conductivity test to differentiate between most diamonds, which are colourless or near colourless, and most moissanite gemstones, when the processor unit determines that the specimen 320 falls under the category of the group consisting of diamond and moissanite.

The method includes a process step of a user holding and positioning a gemstone specimen 320 near or next to the gemstone test apparatus 210.

The test probe 330 is then placed on a table or a major top surface of the specimen 320.

Following this, the electrical conductivity UV light module 335 illuminates the gemstone specimen 320 with light rays with a wavelength of about 365 nm while the test probe 330 is still in contact with the gemstone specimen 320. In a general sense, the light rays can also have a wavelength ranging from about 315 nm to about 425 nm. In a special embodiment, the light rays have a wavelength ranging from about 300 nm to about 430 nm The electrical conductivity UV light module 335 and the head portion of the handheld casing 213 are arranged to allow light rays from the UV light module 335 to reach the gemstone specimen 320 when test probe 330 is in contact with the gemstone specimen 320.

While the specimen 320 is being illuminated with these UV light rays or shortly after the specimen 320 is illuminated with these UV light rays, the electrical conductivity test circuit module 212b receives an electrical voltage signal from the test probe 330 that receives the electrical voltage signal from the surface of the specimen 320.

An electrical current later flow from the electrical conductivity test circuit module 212b, to the conductive housing finger pad 212d, to a finger of a user that is pressing the housing finger pad, to a human body of the user, to another finger of the user, to either a stone rest that is supporting the gemstone specimen 320 or to a ring on which the gemstone specimen 320 is mounted, to the gemstone specimen 320, to the test probe 330, and back to the electrical conductivity test circuit module 212b.

The electrical conductivity test circuit module 212b then measures this electrical current, which relates to the electrical conductivity of the specimen 320.

After this, the electrical conductivity test circuit module 212b sends this electrical current measurement to the processor unit.

The processor unit then determines a category of the specimen 320 according to the electrical current measurement. In other words, the processor unit determines whether the specimen 320 falls under a category of most diamond or under a category of most moissanite, according to the electrical current measurement.

Most moissanite gemstones are electrically conductive while F1 moissanite gemstones have high electrical resistance. On the other hand, most diamonds, which are colourless or near colourless, are not electrically conductive while some lab-grown synthetic diamonds are electrically conductive.

After this, the processor unit sends a signal to the display unit 230 for showing or indicating the category of the specimen 320, which is determined by the processor, to a user. Functionally, the light absorption test unit 211 also provides a first light method to differentiate between colourless or near colourless diamonds and moissanite gemstones.

The method uses a light absorption test, and it is described below.

The method includes a process step of a user holding and positioning a gemstone specimen 320.

A user then holds the handheld casing 213 such that an outer end of the metal tube of the test probe tube 216 is placed on a table or a major flat surface of the gemstone specimen 320. The user then presses the metal tube against the table of the specimen 320.

A spring 250 later acts to bring the metal tube to its initial position when the user stops the pressing of the metal tube against the specimen 320.

The thin film pressure sensor of the pressure-switch 225 can detect when the metal tube is pressing and when the metal tube is not pressing against the specimen 320. The thin film pressure sensor then provides a respective metal tube pressing or contact status signal to the processor unit of the electronic testing unit 228.

The processor unit includes a program or instructions to receive the contact status signal from the thin film pressure sensor of the pressure-switch 225.

The light sources 219a and 219b of the light absorption UV light module 219 are then activated by the processor unit according to the switch position signal. The activated light sources 219a and 219b later produce ultraviolet light rays with a wavelength of about 365 nm for illuminating the abovementioned gemstone specimen 320.

The light absorption UV light module 219 and the head portion of the handheld casing 213 are arranged to allow light rays from the light sources 219a and 219b to reach the gemstone specimen 320, which is placed near the outer end of the metal tube of the test probe tube 216.

The arrangement of these two light sources 219a and 219b allow the table of the specimen 320 to receive light rays from either one light sources 219a and 219b or from both light sources 219a and 219b when the metal tube is placed at different parts of the specimen table.

In practice, the size of the metal tube is often smaller than the size of the specimen table. Because of this, a user may place the metal tube at different parts of the specimen table. The metal tube can be placed near a centre position or near an edge of the specimen table.

When the metal tube is placed substantially near or at the centre location of the specimen table, the specimen table then receives light rays emitted from both light sources 219a and 219b.

When the metal tube is placed substantially near the edge of the specimen 320, the specimen table can still receive light emitted from one of the two light sources 219a and 219b.

In effect, the two light sources 219a and 219b allow the specimen table to receive light rays from at least one of the light sources 219a and 219b even when the metal tube is placed at different parts of the specimen table.

This is different from other gemstone testers, wherein each tester comprises a test probe tube and just one single light source. A specimen may then not receive enough light rays for testing the specimen, which can degrade or affect the testing to the specimen when the test probe is not placed at a centre portion of the table.

Referring to specimen 320, if the specimen 320 refers to a moissanite gemstone, the moissanite gemstone then absorbs these light rays from the light sources 219a and 219b. In other words, essentially no light rays are reflected from the moissanite gemstone.

On the other hand, if the specimen 320 refers to a colourless or near colourless diamond gemstone, the diamond gemstone then reflects all or most of the light rays from the light sources 219a and 219b.

The metal tube of the test probe tube 216 acts as a light guide to receive the light rays reflected from the specimen 320.

The photodiode of the photodetector 221 later detects and measures the intensity of these light rays from the metal tube. The photodetector 221 then sends the light measurements to the processor unit. The photodiode is intended for receiving light rays from the metal tube and not for receiving light rays from other sources.

The processor unit later selects or determines a category of the specimen 320 according to the received light measurements.

In detail, the processor unit determines whether the gemstone specimen 320 falls under a category of colourless or near colourless diamond, or under a category of moissanite in accordance with the light measurements. After this, the processor unit generates a corresponding gemstone category signal and sends the gemstone category signal to the display unit 230.

After this, the processor unit sends a signal to the display unit 230 for showing or indicating the category of the specimen 320, which is determined by the processor, to a user.

Functionally, the light absorption test unit 211 also provides a second light method.

When the processor unit determines, from the first light absorption, that the gemstone specimen 320 falls under the category of a colourless or near colourless diamond, the processor unit automatically starts or performs this further light absorption test.

The second light method is intended to differentiate between a diamond from a first group and a diamond from a second group of diamonds.

The first group consists of type IaA, IaAB, and Ib diamonds. These diamonds are extracted or mined from the ground, and they are not enhanced using high-pressure and high temperature (HPHT) methods.

The second group consists of type IaB, IIa, and IIb diamonds. These diamonds are either extracted and mined from the ground or produced in a laboratory. They can also be enhanced using HPHT methods.

A description of the second light method is provided below.

When the processor unit determines, from the first light absorption, that the gemstone specimen 320 falls under the category of a colourless or near colourless diamond, the processor unit automatically starts this further light absorption test to differentiate between a diamond from the first group and a diamond from the second group.

The method includes a step of the processor unit activating the light sources 219c and 219d of the light absorption UV light module 219 to produce ultraviolet light rays with a wavelength of about 254 nm for illuminating the gemstone specimen 320.

The light absorption UV light module 219 and the head portion of the handheld casing 213 allows light rays from the light sources 219c and 219d to reach the gemstone specimen 320, which is placed near the outer end of the metal tube of the test probe tube 216.

Referring to the specimen 320, if specimen 320 refers to a diamond from the first group, then this diamond will absorb these light rays from the light sources 219c and 219d. In other words, essentially no light rays are reflected from this diamond.

On the other hand, if the specimen 320 refers to a diamond gemstone from the second group, then this diamond will reflect all or most of the light rays from the light sources 219a and 219d.

The metal tube of the test probe tube 216 receives any light rays reflected from the specimen 320.

The photodiode of the photodetector 221 later detects and measures the intensity of these light rays from the metal tube.

The processor unit then determines a category of the specimen 320 in accordance with the light measurements. The processor unit selects or determines whether the gemstone specimen 320 falls under a category of diamond from the first group or under a category of diamond from the second group in accordance with the light measurements.

After this, the processor unit generates a corresponding gemstone category signal and sends the gemstone category signal to the display unit 230.

With reference to the display unit 230, it later shows and indicates the category selected by the processor unit to the user.

In one example, a LCD of the display unit 230 can be activated for showing that the gemstone testing apparatus 210 detects diamond. The LCD of the display unit 230 can be activated for showing that the gemstone testing apparatus 210 detects moissanite. The LCD of the display unit 230 can be activated for showing that the gemstone testing apparatus 210 detects diamond from a first group consisting of type IaA, IaB, and IB diamonds. The LCD of the display unit 230 can be activated for showing that the gemstone testing apparatus 210 detects diamond from a second group consisting of type IaB, IIa, and IIb diamonds.

The buzzer 292 also is intended for receiving a signal from the processor unit and generating a corresponding audio sound to alert the user.

The power socket connector 310 is intended for receiving electrical power from an external power source 314 and for transferring this electrical power to the battery charger 312.

The battery charger 312 then converts a voltage of the electrical power to another voltage that is suitable for the battery module 305. The battery charger 312 later transfers this converted electrical power to the battery module 305.

The battery module 305 stores this electrical power and afterwards supplies the stored electrical power to the voltage regulator 307.

The voltage regulator 307 then provides electrical power with a voltage that falls within a predetermined regulated range to the UV light module 219 and to the photodetector 221, which are both activated and controlled by the light absorption test unit 211.

The voltage regulator 307 also supplies this electrical power to the electrical conductivity UV light module 335, which is activated and controlled by the heater control and driver circuit 212a-1, the electrical conductivity test circuit module 212b, and the metal detector circuit 212c.

The voltage regulator 307 also supplies this electrical power to the processor unit of the electronic testing unit 228, which controls the display unit 230, and the buzzer 292.

In a general sense, the gemstone testing apparatus 210 can include, not just two, but include just one or more first light sources that produce UV light rays with a wavelength of about 365 nm. The gemstone testing apparatus 210 can also include, not just two, but include just one or more second light sources that produce UV light rays with a wavelength of about 254 nm.

Several implementations are possible.

In one implementation, the gemstone testing apparatus 210 includes two first light sources and two second light sources. In a further implementation, the gemstone testing apparatus 210 includes two first light sources and one second light source. In another implementation, the gemstone testing apparatus 210 includes one first light source and two second light sources. In a further implementation, the gemstone testing apparatus 210 comprises one first light source and one second light source.

The gemstone testing apparatus provides several benefits.

The gemstone testing apparatus enables the user to obtain parameters of a gemstone specimen with a single gemstone test unit. This is useful as the different parameters allow a category of the specimen to be determined with greater accuracy and efficiency. In other words, the material of the specimen can be determined with higher confidence.

The gemstone testing apparatus also allows different test units, namely the thermal and/or the electrical conductivity test unit and the light absorption unit test, to share common parts, such as computing processor unit and display unit.

This is different from an arrangement of two gemstone testing devices, one providing thermal and/or the electrical conductivity test and another providing light absorption test. The testing is longer because the user needs to switch from one testing device to another testing device. The arrangement also does not allow sharing of common parts and is thus cost more. Such an arrangement is also bigger and is thus less convenient to carry around.

Regarding the thermal conductivity, most diamonds are extremely efficient thermal conductors. Diamonds conduct heat well because they have carbon atoms that are linked strong covalent bonds, these carbon atoms are part of a diamond crystal. For instance, the thermal conductivity of natural diamond is around 22 W/(cm·K), which makes the natural diamond five times better at conducting heat than copper.

Moissanite is a crystalline form of silicon carbide that resembles a diamond. Moissanite and diamond have comparable thermal conductivities.

Simulant, such as cubic zirconia and sapphire, can be distinguished from a group consisting of diamond and moissanite by comparing their thermal conductivity properties.

Regarding the electrical conductivity, most diamonds, which are colourless or near colourless, are not electrically conductive. Some lab-grown synthetic diamonds are electrically conductive. The synthetic diamonds are produced using some impurities which cause these synthetic diamonds to have an electrical conductivity that is similar to the semiconductor material.

Most moissanite gemstones are electrically conductive. Moreover, the electrical resistance of an F1 moissanite gemstone is higher than normal moissanite. In addition, the electrical resistance varies on different surface areas of the F1 Moissanite gemstone.

Colourless or near colourless diamonds can be distinguished from most moissanite by comparing their electrical conductivity.

Some lab grown synthetic diamonds are electrically conductive while some moissanites are also electrically conductive. Hence, the electrical conductivity may not be able to differentiate between certain diamonds and certain moissanite.

Regarding the light absorption test, colourless or near colourless diamonds can be distinguished from moissanite by comparing their light absorption of light rays with a fixed wavelength of about 365 nm.

A gemstone specimen from a first group consisting of type IaA, IaAB, and Ib diamonds can also be distinguished from a gemstone specimen from a second group consisting of type IaB, IIa, and IIb diamonds by comparing their light absorption of light rays with a fixed wavelength of about 254 nm.

This tester has a pen-like shape with a first probe and a second probe, both probes being provided at one end of the tester.

The first probe is intended to perform a thermal conductivity test and a metal detector test. The thermal conductivity test can separate simulant from a group consisting of diamond and moissanite.

The first probe can also provide an electrical conductivity test, wherein the electrical conductivity test is performed together with ultraviolet light rays with a wavelength of about 365 nm, although this electrical conductivity test, in some examples, is not omitted. The electrical conductivity test can separate colourless or near colourless diamond from most moissanite.

The second probe is intended to perform a first light absorption test with light rays with a wavelength of about 365 nm. This light absorption test can separate moissanite from colourless or near colourless diamonds.

The second probe can also provide a second light absorption test with light rays with a wavelength of a wavelength of about 254 nm. The light absorption test can separate diamonds from the first group from diamonds from the second group.

FIG. 21 shows an electronic block diagram of a combination gemstone testing apparatus 210', which a variant of the combination gemstone testing apparatus 210 of FIG. 14.

The gemstone testing apparatus 210' includes most parts of the gemstone testing apparatus 210, which are described above, except for the electrical conductivity test circuit module 212b of the gemstone testing apparatus 210.

The combination gemstone testing apparatus 210' includes an elongated handheld casing 213 with an electrical test circuit and a display unit 230.

The electrical test circuit includes a test probe 330, a thermal conductivity test unit 212', a light absorption electrical test unit 211, and supporting electronics.

The supporting electronics includes an electronic testing unit 228, a buzzer 292, and a power source unit 233.

Referring to the thermal conductivity test unit 212', it includes a test probe 330, a conductivity test module, and a conductive housing finger pad 212d. The conductivity test module comprises a thermal conductivity test circuit module 212a and a metal detector circuit 212c. The metal detector circuit 212c is electrically connected to the housing finger pad 212d.

The embodiments can also be described with the following lists of features or elements being organized into an item list. The respective combinations of features, which are disclosed in the item list, are regarded as independent subject matter, respectively, that can also be combined with other features of the application.

A feature list for a thermal and electrical conductivity gemstone testing apparatus is shown below.
1. A thermal and electrical conductivity gemstone testing apparatus comprising
   an apparatus body, the apparatus body enclosing an electronic circuit,
   a ultraviolet light (UVL) [or visible violet light (VVL)] emitter for generating ultraviolet light rays,
   a reflector housing,
   a transparent housing portion, the transparent housing portion being transparent for ultraviolet light rays, the transparent housing portion being provided adjacent to the reflector housing,
   a detector probe, the detector probe protruding from the transparent housing portion,
   wherein the ultraviolet light emitter is provided within the reflector housing and the reflector housing is provided for directing the ultraviolet light of the ultraviolet light emitter through the transparent housing portion into the vicinity of a tip of the detector probe, and
   wherein the detector probe and the ultraviolet light emitter are connected to the electronic circuit, the electronic circuit comprising a thermal and electrical conductivity sensing circuitry that is connected to the detector probe and to a processing unit, the processing unit being operative to turn on the ultraviolet light emitter and to perform a subsequent conductivity measurement using the thermal and electrical conductivity sensing circuitry.
2. The thermal and electrical conductivity gemstone testing apparatus of item 1, wherein
   the ultraviolet light emitter capable of emitting light rays with a wavelength of about 315 nm to about 425 nm.
3. The thermal and electrical conductivity gemstone testing apparatus of one of the items 1 to 2, wherein
   the detector probe is provided at an end portion of the transparent housing portion.
4. The thermal and electrical conductivity gemstone testing apparatus according to one of the preceding items,
   wherein a reflective layer is provided (by electroplating) for concentrating the light rays.
5. The thermal and electrical conductivity gemstone testing apparatus according to one of the preceding items, the gemstone testing apparatus comprising a display region that is connected to the processing unit.
6. The thermal and electrical conductivity gemstone testing apparatus according to item 5, wherein the display region comprises indicator LEDs or LCDs.
7. The thermal and electrical conductivity gemstone testing apparatus according to one of the preceding items, wherein
   the transparent housing portion is conically tapered from the reflector housing towards a tip end of the transparent housing portion.
8. The thermal and electrical conductivity gemstone testing apparatus according to one of the preceding items further comprising
   a power source unit for supplying electrical power to the thermal and electrical conductivity gemstone testing apparatus.
9. The thermal and electrical conductivity gemstone testing apparatus according to one of the preceding items further comprising
   a buzzer for providing an audio indication of a gemstone test result.
10. A head portion for a thermal and electrical conductivity gemstone testing apparatus, the head portion comprising
    a reflector housing,
    a transparent housing portion, the transparent housing portion being attached to the reflector housing, the transparent housing portion being transparent for ultraviolet light rays, and
    a detector probe (or tube), the detector probe protruding from the transparent housing portion, the detector probe having connections for connecting to an electronic circuit of the gemstone testing apparatus.
11. The head portion of item 9, comprising an ultraviolet light emitter being provided within the reflector housing, and the ultraviolet light emitter having connections for connecting to the electronic circuit.
12. A method for producing a thermal and electrical conductivity gemstone testing apparatus, the method comprising
    providing a transparent housing portion with a detector probe,
    attaching the transparent housing portion to the reflector housing,
    providing an apparatus body,
    connecting an ultraviolet light emitter to an electronic circuit of the apparatus body,
    connecting the detector probe to the electronic circuit,
    attaching the reflector housing to the apparatus body.

The embodiments can also be described with the following lists of features or elements being organized into an item list. The respective combinations of features, which are disclosed in the item list, are regarded as independent subject matter, respectively, that can also be combined with other features of the application.
1. A gemstone testing apparatus for testing a gemstone specimen, the gemstone testing apparatus comprising a handheld casing,
a processor unit being enclosed in the handheld casing,
a first gemstone test device comprising
   a first test probe for contacting a table of the gemstone specimen, and
   a thermal conductivity test module comprising
      a heating element being electrically connected to the first test probe for heating the first test probe,
      a temperature measurement unit being electrically connected to the first test probe for measuring a thermal conductivity of the specimen,
      wherein the processor unit is adapted to determine a first category of the specimen according to the thermal conductivity measurement,
a second gemstone test device comprising
   a second test probe for contacting the table of the specimen,
   a light absorption module comprising
      at least two first light sources for emitting first light rays with a wavelength of about 365 nm to illuminate an area that is in the vicinity of an outer end of the second test probe, the at least two first light sources being provided adjacent to the second test probe, the second test probe comprises a light guide for receiving the first light rays that are reflected from the specimen and for transmitting the first light rays to an inner end of the second test probe,
      a photodetector being provided at the inner end of the second test probe to measure light intensity of the first light rays, wherein the processor unit is adapted to determine a second category of the specimen according to the light intensity measurement of the first light rays,
      at least two second light sources for emitting second light rays with a wavelength of about 254 nm to illuminate an area that is in the vicinity of the outer end of the second test probe, the at least two second light sources being provided adjacent to the second test probe, the light guide being provided for receiving the second light rays that are reflected from the specimen and for transmitting the second light rays to the inner end of the second test probe, and
      the photodetector being provided to measure light intensity of the second light rays, wherein the processor unit is adapted to determine a third category of the specimen according to the light intensity measurement of the second light rays, and
a display unit being attached to the handheld casing for displaying a category of the specimen, which is determined by the processor unit.

2. The gemstone testing apparatus according to item 1, wherein
the first gemstone test device further comprises an electrical conductivity test module comprising
   a third light source for emitting third light rays with a wavelength of about 365 nm to illuminate an area that is in the vicinity of an outer end of the first test probe, and
   an electrical conductivity test circuit being electrically connected to the first test probe for measuring an electrical conductivity of the specimen,
wherein
the processor unit is adapted to determine a fourth category of the specimen according to the electrical conductivity measurement.

3. The gemstone testing apparatus according to item 1 or 2, wherein
the first test probe protrudes from a transparent housing portion, which is provided at one end portion of the handheld casing.

4. The gemstone testing apparatus according to one of the above-mentioned items, wherein
the third light source emits light rays with a wavelength of between about 315 nm and about 425 nm.

5. The gemstone testing apparatus according to one of the above-mentioned items, wherein
the at least two first light sources comprises two first light sources and the at least two second light sources comprises two second light sources.

6. The gemstone testing apparatus according to one of the above-mentioned items, wherein
the first light sources and the second light sources are arranged around the second test probe in a symmetric manner.

7. The gemstone testing apparatus according to one of the above-mentioned items, wherein
the first light sources emit light rays with a wavelength of between about 315 nm and about 400 nm.

8. The gemstone testing apparatus according to one of the above-mentioned items, wherein
the second gemstone test device comprises
   a pressure switch, and
   a pressure transmitting means for transferring a force from the second test probe to the pressure switch, wherein the pressure switch transmits a switch status signal for activating the second gemstone test device.

9. The gemstone testing apparatus according to item 8, wherein
the pressure switch comprises a thin film pressure sensor or a micro-switch.

10. The gemstone testing apparatus according to one of the above-mentioned items, wherein
the light guide comprises a hollow metal tube, or an optical fibre, or both.

11. The gemstone testing apparatus according to one of the above-mentioned items further comprising
an external cap being attachable to the handheld casing for protecting the first test probe and the second test probe.

12. The gemstone testing apparatus according to item 11, wherein
the external cap comprises a gemstone test reference tablet that is provided for checking functions of the light absorption gemstone testing apparatus.

13. The gemstone testing apparatus according to one of the above-mentioned items further comprising
a power source unit for supplying electrical power to the processor unit, the first gemstone test device gemstone testing apparatus, and the second gemstone test device gemstone testing apparatus.

14. The gemstone testing apparatus according to one of the above-mentioned items, wherein
the display unit comprises a Liquid Crystal Display (LCD) display panel for displaying a category of the specimen, which is determined by the processor unit.

15. The gemstone testing apparatus according to one of the above-mentioned items further comprising a buzzer for providing an audio indication of a category of the specimen, which is determined by the processor unit, to a user.

16. A method for testing a gemstone specimen, the method comprising
    heating the first test probe,
    pressing a first test probe of a gemstone testing apparatus against the gemstone specimen,
    measuring a thermal conductivity of the specimen,
    determining a first category of the specimen according to the thermal conductivity measurement,
    pressing a second test probe of a gemstone testing apparatus against the gemstone specimen,
    activating at least two first light sources of the gemstone testing apparatus for emitting first light rays with a wavelength of about 365 nm to illuminate an area that is in the vicinity of an outer end of the second test probe,
    measuring a first light intensity of the first light rays that are reflected from the gemstone specimen, and
    determining a second category of the gemstone specimen in accordance with the measured first light intensity.
    activating at least two second light sources of the gemstone testing apparatus for emitting second light rays with a wavelength of about 254 nm to illuminate an area that is in the vicinity of an outer end of the second test probe,
    measuring a second light intensity of the second light rays being reflected from the gemstone specimen, and
    determining a third category of the gemstone specimen in accordance with the measured second light intensity.

17. The method according to item 16 further comprising
    activating a third light source of the gemstone testing apparatus for emitting third light rays with a wavelength of about 365 nm to illuminate an area that is in the vicinity of an outer end of the first test probe,
    measuring an electrical conductivity of the specimen, and
    determining a fourth category of the gemstone specimen in accordance with the electrical conductivity measurement.

18. The method according to item 16 or 17 further comprising providing an indication of the material of the gemstone specimen to a user.

19. The method according to item 18, wherein the provision of the indication of the material of the gemstone specimen comprises providing a visual indication of the material of the gemstone specimen.

20. The method according to item 18 or 19, wherein the provision of the indication of the material of the gemstone specimen comprises providing an audio indication of the material of the gemstone specimen.

Although the above description contains many specificities, these should not be construed as limiting the scope of the embodiments but merely providing an illustration of the foreseeable embodiments. Especially the above-stated advantages of the embodiments should not be construed as limiting the scope of the embodiments but merely to explain possible achievements if the described embodiments are put into practice. Thus, the scope of the embodiments should be determined by the claims and their equivalents, rather than by the examples that are given.

REFERENCE NUMBERS 10 light absorption gemstone testing apparatus
13 elongated handheld casing
14 power on button
16 test probe
19 light module
21 photodetector
25 pressure switch
28 electronic testing unit
30 display unit
33 power source unit
36 elongated hollow body portion
36a first end of the elongated hollow body portion
36b second end of the elongated hollow body portion
38 head portion
40 spring support unit
42 hollow conical member of the head portion
44 actuator member of the head portion
47 support member
50 coil torsion springs
52 mechanical micro-switch
55 rectangular body
57 offset lever
59 single throw and single pole (STSP) switch
62 electrical terminals
65 on/off button
68 metal tube
68a first end of the metal tube
68b second end of the metal tube
70 reflective inner surface
74 protective shell
76 cavity formed by the protective shell
78 light source
78' border of light rays
80 light source
81 transparent cover
84 photodiode
89 indicator lights
92 buzzer
96 current limiting resistors
102 processor unit
105 battery module
107 voltage regulator
108 low battery indicator
110 power socket connector
112 battery charger
114 external power source
120 specimen
120a table of the specimen
120b side facet of the specimen
121 external cap
121a outer surface
122 fool-proof test disc
122a layer
122b layer
130 flow chart
133 step
136 step
140 step
143 step
146 step
149 step
152 step
155 step
160 step
163 step
210 combination gemstone testing apparatus
210' gemstone testing apparatus
211 light absorption test unit
211a reflectivity electrical circuit
211b LED driver 212 thermal and electrical conductivity test unit
212' thermal conductivity test unit
212a thermal conductivity test circuit module
212a-1 heater control and driver circuit
212a-2 thermocouple amplifier circuit
212b electrical conductivity test circuit module
212c metal detector circuit
212d conductive housing finger pad
213 handheld casing
214 power on button
216 test probe tube
219 light absorption UV light module
219a light source
219b light source
219c light source
219d light source
221 photodetector
225 probe pressure-switch
228 electronic testing unit
230 display unit
231 external cap
233 power source unit
250 spring
292 buzzer
310 power socket connector
312 battery charger
305 battery module
307 voltage regulator
314 external power source
320 specimen
330 test probe
335 electrical conductivity UV light module
337 spring element
340 stone rest
342 recessed area

The invention claimed is:

1. A gemstone testing apparatus for testing a gemstone specimen, the gemstone testing apparatus comprising:
   a handheld casing;
   a processor unit being enclosed in the handheld casing;
   a first gemstone test device comprising
      a first test probe for contacting a table of the gemstone specimen, and
      a thermal conductivity test module comprising
         a heating element being electrically connected to the first test probe for heating the first test probe,
         a temperature measurement unit being electrically connected to the first test probe for measuring a thermal conductivity of the specimen,
      wherein the processor unit is adapted to determine a first category of the specimen according to the thermal conductivity measurement;
   a second gemstone test device comprising
      a second test probe for contacting the table of the specimen,
      a light absorption module comprising
         at least two first light sources for emitting first light rays with a wavelength of about 365 nm to illuminate an area that is in the vicinity of an outer end of the second test probe, the at least two first light sources being provided adjacent to the second test probe, the second test probe comprises a light guide for receiving the first light rays that are reflected from the specimen and for transmitting the first light rays to an inner end of the second test probe,
         a photodetector being provided at the inner end of the second test probe to measure light intensity of the first light rays, wherein the processor unit is adapted to determine a second category of the specimen according to the light intensity measurement of the first light rays,
         at least two second light sources for emitting second light rays with a wavelength of about 254 nm to illuminate an area that is in the vicinity of the outer end of the second test probe, the at least two second light sources being provided adjacent to the second test probe, the light guide being provided for receiving the second light rays that are reflected from the specimen and for transmitting the second light rays to the inner end of the second test probe, and the photodetector being provided to measure light intensity of the second light rays, wherein the processor unit is adapted to determine a third category of the specimen according to the light intensity measurement of the second light rays; and
   a display unit being attached to the handheld casing for displaying a category of the specimen, which is determined by the processor unit.

2. The gemstone testing apparatus according to claim 1, wherein the first gemstone test device further comprises an electrical conductivity test module comprising:
   a third light source for emitting third light rays with a wavelength of about 365 nm to illuminate an area that is in the vicinity of an outer end of the first test probe, and
   an electrical conductivity test circuit being electrically connected to the first test probe for measuring an electrical conductivity of the specimen; and
   wherein the processor unit is adapted to determine a fourth category of the specimen according to the electrical conductivity measurement.

3. The gemstone testing apparatus according to claim 2, wherein the third light source emits light rays with a wavelength of between about 315 nm and about 425 nm.

4. The gemstone testing apparatus according to claim 1, wherein the first test probe protrudes from a transparent housing portion, which is provided at one end portion of the handheld casing.

5. The gemstone testing apparatus according to claim 1, wherein the at least two first light sources comprise two first light sources and the at least two second light sources comprises two second light sources.

6. The gemstone testing apparatus according to claim 1, wherein the first light sources and the second light sources are arranged around the second test probe in a symmetric manner.

7. The gemstone testing apparatus according to claim 1, wherein the first light sources emit light rays with a wavelength of between about 315 nm and about 400 nm.

8. The gemstone testing apparatus according to claim 1, wherein the second gemstone test device comprises:
   a pressure switch; and
   a pressure transmitting means for transferring a force from the second test probe to the pressure switch, wherein the pressure switch transmits a switch status signal for activating the second gemstone test device.

9. The gemstone testing apparatus according to claim 8, wherein the pressure switch comprises a thin film pressure sensor or a micro-switch.

10. The gemstone testing apparatus according to claim 1, wherein the light guide comprises one or more of a hollow metal tube and an optical fibre.

11. The gemstone testing apparatus according to claim 1, further comprising an external cap being attachable to the handheld casing for protecting the first test probe and the second test probe.

12. The gemstone testing apparatus according to claim 11, wherein the external cap comprises a gemstone test reference tablet that is provided for checking functions of the light absorption module of the gemstone testing apparatus.

13. The gemstone testing apparatus according to claim 1, further comprising a power source unit for supplying electrical power to the processor unit, the first gemstone test device, and the second gemstone test device.

14. The gemstone testing apparatus according to claim 1, wherein the display unit comprises a Liquid Crystal Display (LCD) display panel for displaying the category of the specimen, which is determined by the processor unit.

15. The gemstone testing apparatus according to claim 1, further comprising a buzzer for providing an audio indication of the category of the specimen, which is determined by the processor unit, to a user.

16. A method for testing a gemstone specimen, the method comprising:
heating a first test probe;
pressing the first test probe of a gemstone testing apparatus against the gemstone specimen;
measuring a thermal conductivity of the specimen;
determining a first category of the specimen according to the thermal conductivity measurement;
pressing a second test probe of a gemstone testing apparatus against the gemstone specimen;
activating at least two first light sources of the gemstone testing apparatus for emitting first light rays with a wavelength of about 365 nm to illuminate an area that is in the vicinity of an outer end of the second test probe;
measuring a first light intensity of the first light rays that are reflected from the gemstone specimen;
determining a second category of the gemstone specimen in accordance with the measured first light intensity;
activating at least two second light sources of the gemstone testing apparatus for emitting second light rays with a wavelength of about 254 nm to illuminate an area that is in the vicinity of an outer end of the second test probe;
measuring a second light intensity of the second light rays being reflected from the gemstone specimen; and
determining a third category of the gemstone specimen in accordance with the measured second light intensity.

17. The method according to claim 16, further comprising:
activating a third light source of the gemstone testing apparatus for emitting third light rays with a wavelength of about 365 nm to illuminate an area that is in the vicinity of an outer end of the first test probe;
measuring an electrical conductivity of the specimen; and
determining a fourth category of the gemstone specimen in accordance with the electrical conductivity measurement.

18. The method according to claim 16, further comprising providing an indication of the material of the gemstone specimen to a user.

19. The method according to claim 18, wherein the provision of the indication of the material of the gemstone specimen comprises providing a visual indication of the material of the gemstone specimen.

20. The method according to claim 18, wherein the provision of the indication of the material of the gemstone specimen comprises providing an audio indication of the material of the gemstone specimen.

* * * * *